(12) United States Patent
Chen et al.

(10) Patent No.: US 12,214,043 B2
(45) Date of Patent: Feb. 4, 2025

(54) THERAPEUTIC NANOMATERIALS

(71) Applicant: University of Connecticut, Farmington, CT (US)

(72) Inventors: Yupeng Chen, Farmington, CT (US); Jinhyung Lee, Farmington, CT (US); Wuxia Zhang, Farmington, CT (US)

(*) Notice: Subject to any disclaimer, the term of this patent is extended or adjusted under 35 U.S.C. 154(b) by 119 days.

(21) Appl. No.: 17/514,390

(22) Filed: Oct. 29, 2021

(65) Prior Publication Data

US 2022/0133893 A1 May 5, 2022

Related U.S. Application Data

(60) Provisional application No. 63/106,934, filed on Oct. 29, 2020.

(51) Int. Cl.
*A61K 47/54* (2017.01)
*A61K 31/194* (2006.01)
(Continued)

(52) U.S. Cl.
CPC .......... *A61K 47/545* (2017.08); *A61K 31/194* (2013.01); *A61K 31/51* (2013.01); *A61K 31/519* (2013.01); *A61K 31/721* (2013.01); *A61K 31/722* (2013.01); *A61K 31/727* (2013.01); *A61K 31/728* (2013.01); *A61K 38/19* (2013.01);
(Continued)

(58) Field of Classification Search
CPC .......... G02F 1/133334; G02F 1/13452; H01L 27/124; H01Q 1/243; H01Q 1/52; H05K 7/20963; H05K 9/0081; A61K 47/545; A61K 45/06; A61K 47/542; A61K 47/6925; A61K 31/519; A61K 31/194; A61K 31/51; A61K 31/721; A61K 31/722; A61K 31/727; A61K 31/728; A61K 38/19; A61K 38/363; A61K 38/385; A61K 38/40; A61K 47/549; A61K 47/62; A61K 47/65; A61K 47/6929; A61K 47/6949; A61K 47/6957; A61K 49/0095; A61K 9/0019; A61K 9/0092; A61K 9/08; A61K 9/5123; A61K 9/5146; A61L 2300/252; A61L 2300/414; A61L 2400/12; A61L 27/227; A61L 27/54; A61L 2300/406; A61L 27/20; A61L 27/50; A61L 27/52; A61L 2300/236; A61L 2300/258; A61L 2300/624; A61L 2300/802; A61L 2400/06; A61L 27/12; A61L 27/225; A61L 27/24; A61L 27/3633; A61L 27/3645; A61L 27/3675

See application file for complete search history.

(56) References Cited

U.S. PATENT DOCUMENTS 9,775,842 B2 * 10/2017 Chen .................. A61K 9/08
10,364,440 B2 7/2019 Webster et al.
(Continued)

FOREIGN PATENT DOCUMENTS

WO 2016081522 A1 5/2016
WO 2019191151 A1 10/2019

*Primary Examiner* — Savitha M Rao
(74) *Attorney, Agent, or Firm* — Feeney IP Law; Alan F. Feeney

(57) ABSTRACT

Disclosed herein is a delivery vehicle based on DNA-inspired Janus based nanotubes (JBNTs) for anti-viral treatment. The nanoparticles (NPs) are based the JBNTs conjugated with targeting moieties such as small molecules, aptamers, and peptides.

2 Claims, 10 Drawing Sheets
(10 of 10 Drawing Sheet(s) Filed in Color)
Specification includes a Sequence Listing.

(51) Int. Cl.
  *A61K 31/51*   (2006.01)
  *A61K 31/519*  (2006.01)
  *A61K 31/721*  (2006.01)
  *A61K 31/722*  (2006.01)
  *A61K 31/727*  (2006.01)
  *A61K 31/728*  (2006.01)
  *A61K 38/19*   (2006.01)
  *A61K 38/36*   (2006.01)
  *A61K 38/38*   (2006.01)
  *A61K 38/40*   (2006.01)
  *A61K 47/65*   (2017.01)
  *A61K 47/69*   (2017.01)
  *A61P 31/12*   (2006.01)

(52) U.S. Cl.
  CPC .......... *A61K 38/363* (2013.01); *A61K 38/385* (2013.01); *A61K 38/40* (2013.01); *A61K 47/65* (2017.08); *A61K 47/6929* (2017.08); *A61P 31/12* (2018.01)

(56) References Cited

U.S. PATENT DOCUMENTS

| | | |
|---|---|---|
| 10,555,948 B2 | 2/2020 | Chen et al. |
| 2012/0171121 A1* | 7/2012 | Webster ............. A61K 49/0002 977/788 |

* cited by examiner

FIG. 2a 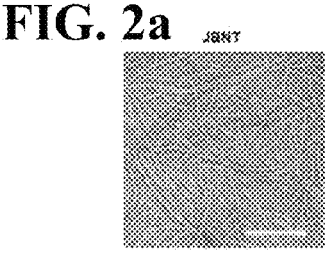 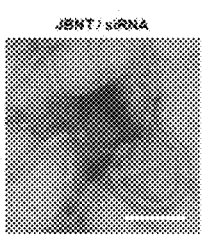 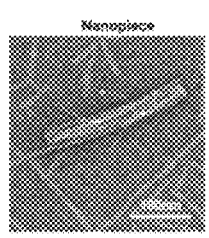 FIG. 2b 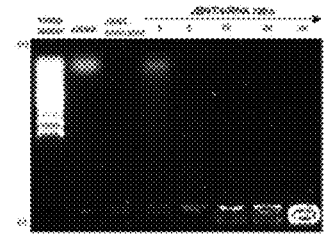
FIG. 2c 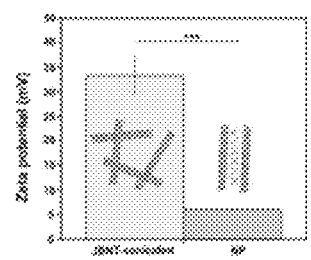 FIG. 2d 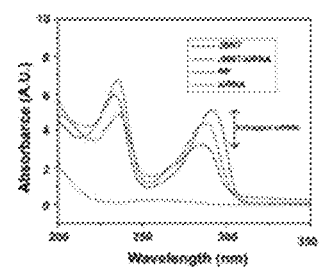
FIG. 2e 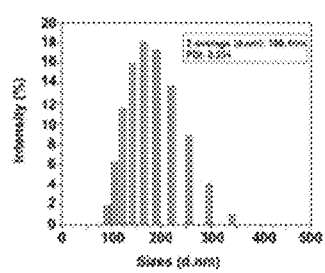 FIG. 2f

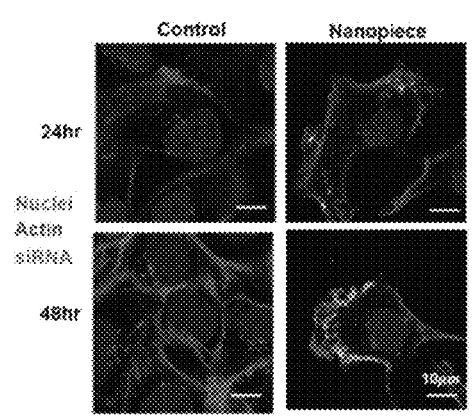
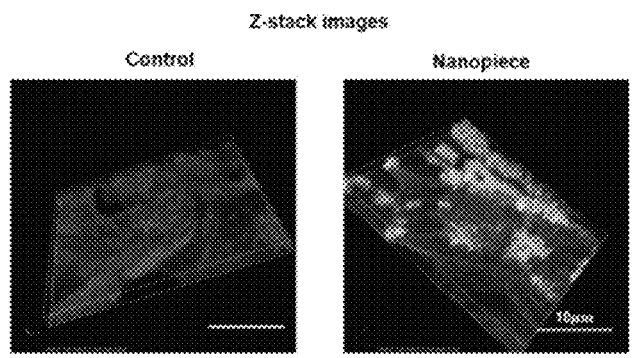
FIG. 3a  FIG. 3b

FIG. 4a
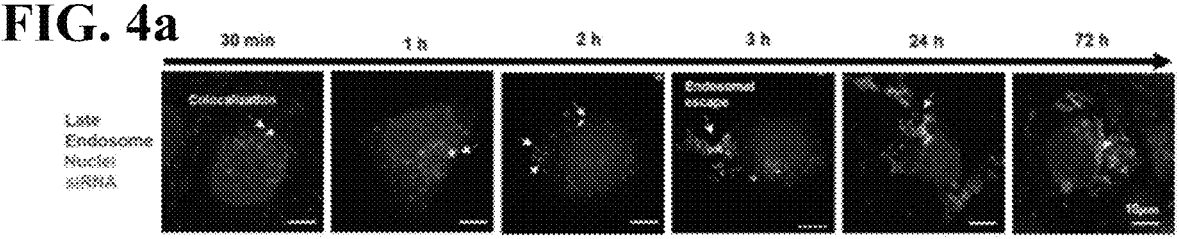
FIG. 4b
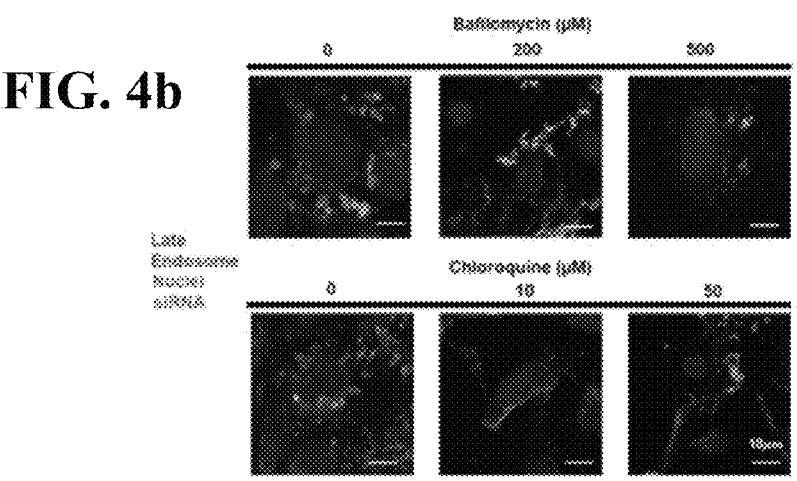
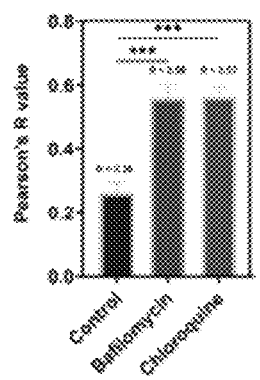
FIG. 4c pH 8.6 pH 7.7 pH 6.8 control

THERAPEUTIC NANOMATERIALS

CROSS-REFERENCE TO RELATED APPLICATION

This application claims priority to U.S. Provisional Patent Application No. 63/106,934, filed Oct. 29, 2020, which is incorporated by reference herein its entirety.

STATEMENT OF GOVERNMENT SUPPORT

This invention was made with government support under Grant Nos. AR072027 and AR069383-04 awarded by the National Institutes of Health (NIH) and Grant No. 1905785 awarded by the National Science Foundation (NSF). The government has certain rights in the invention.

SEQUENCE LISTING

The Instant Application contains a Sequence Listing which has been submitted electronically in ASCII format and is hereby incorporated by reference in its entirety. Said ASCII copy, created on Monday, Dec. 13, 2021 is named "UCT0276US3_ST25 Sequence List TXT" and is 14,391 bytes in size.

BACKGROUND

RNAs (such as siRNAs) are delivered in various ways such as by virus vectors or encapsulation in synthetic vehicles, such as cationic polymers or nanoparticles. siRNAs can be conjugated to cell penetrating peptides or specific antibodies against the infected cell. Viral vectors delivering siRNA have been reported to treat HIV and hepatitis B and C. Clinical trials of siRNA delivery via viral vectors (lentivirus) have been conducted in HIV patients. Recently, the Arbutus Biopharma Corporation reported the efficacious anti-viral treatment of macaques in the early stage of infection by Ebola using a lipid nanoparticle (LNP) injection with siRNA. Arrowhead Pharmaceuticals showed a promising polymeric delivery vehicle (Dynamic PolyConjugates, DPC™) to combat chronic HBV.

Accordingly, novel delivery vehicles for therapeutic agents (e.g., siRNA) are needed.

SUMMARY

Disclosed herein is a delivery vehicle based on DNA-inspired Janus based nanotubes (JBNTs) for anti-viral treatment. The nanoparticles (NPs) are based on the JBNTs conjugated with targeting moieties such as small molecules, aptamers, and peptides, referred to herein as NPs or JBNPs.

Herein, JBNTs are shown to deliver short interfering RNAs (siRNA)s efficiently by escaping endosomes and effectively inhibiting the expression of viral genes in the infected cells. JBNTs can also pre-deliver siRNAs to protect the tissues/cells from virus. Noticeably, the NPs exhibit significantly lower cytotoxicity compared to conventional vehicles.

In some embodiments, disclosed herein is a composition comprising a compound of Formula (I):

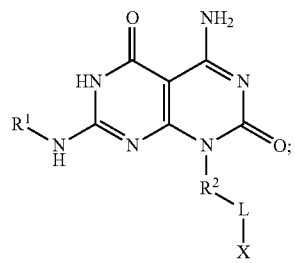

or a pharmaceutically acceptable salt thereof, wherein:
$R^1$ is H or $CH_3$; $R^2$ is $(CH_2)_j$, $(CH_2CH_2O)_k$ or $(CH_2CH_2NH)_m$;
j, k, and m are each independently 0-200;
L is absent or a linker group; and
X is a therapeutic agent.

In some embodiments, disclosed herein is a composition comprising a compound of Formula (II):

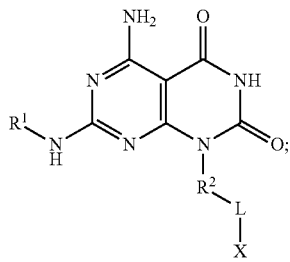

or a pharmaceutically acceptable salt thereof, wherein:
$R^1$ is H or $CH_3$; $R^2$ is $(CH_2)_j$, $(CH_2CH_2O)_k$ or $(CH_2CH_2NH)_m$;
j, k, and m are each independently 0-200;
L is absent or a linker group; and
X is a therapeutic agent.

In some embodiments, disclosed herein is a composition comprising a compound of Formula (III):

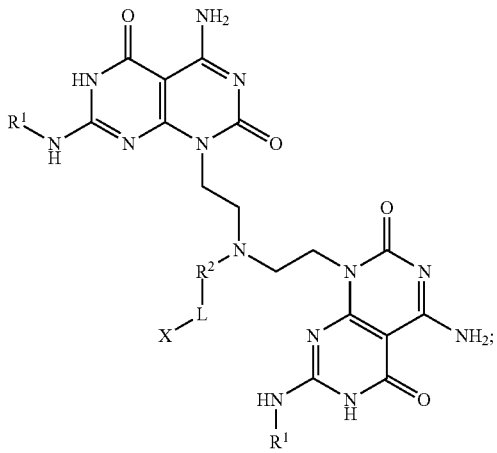

or a pharmaceutically acceptable salt thereof, wherein:
$R^1$ is H or $CH_3$; $R^2$ is $(CH_2)_j$, $(CH_2CH_2O)_k$ or $(CH_2CH_2NH)_m$;

j, k, and m are each independently 0-200;
L is absent or a linker group; and
X is a therapeutic agent.

In some embodiments, disclosed herein is a composition comprising a compound of Formula (IV):

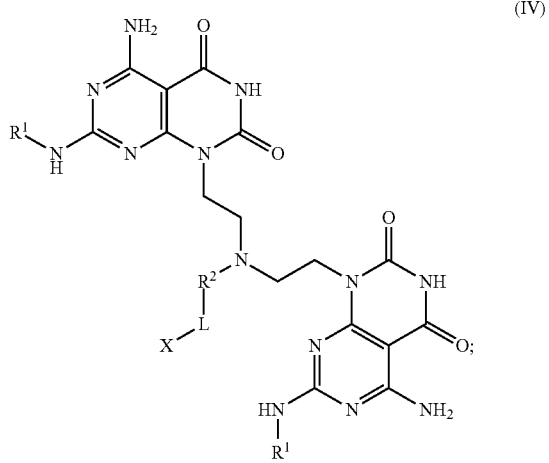

(IV)

or a pharmaceutically acceptable salt thereof, wherein:
R¹ is H or CH₃;
R² is (CH₂)ⱼ, (CH₂CH₂O)ₖ, or (CH₂CH₂NH)ₘ;
j, k, and m are each independently 0-200;
L is absent or a linker group; and
X is a therapeutic agent.

In some embodiments of the composition comprising a compound of any one of Formulas (I)-(IV), L is absent. In other embodiments, L is a linker group.

In some embodiments of the composition comprising a compound of any one of Formulas (I)-(IV), the linker group is selected from an acid cleavable linkage, a reducible disulfide linkage, and a stimuli linker.

In some embodiments of the composition comprising a compound of any one of Formulas (I)-(IV), the linker is an acid cleavable linkage selected from N-acyl hydrazone, carbonate, and ester.

In some embodiments of the composition comprising a compound of any one of Formulas (I)-(IV), the linker is a reducible disulfide linkage selected from N-succinimidyl-4-(2-pyridyldithio)pentanoate (SPP), N-succinimidyl-4-(2-pyridyldithio)butyrate (SPDB), 4-(4'-acetylphenoxy)butanoic acid (AcBut) linkers, dipeptide Val-Cit and Phe-Lys type linker, α-methyl substitution on disulfide linker, two-methyl groups on disulfide linker, engineered cysteine residue, and maytansinoid thiol.

In some embodiments of the composition comprising a compound of any one of Formulas (I)-(IV), the linker is a stimuli linker selected from a trans-cyclooctene linker, a thioether-containing linker, an enzyme cleavable linker, a Val-Cit-PABC containing linker, a Glu-Val-Cit-containing linker, and a Val-Ala containing linker.

In some embodiments of the composition comprising a compound of any one of Formulas (I)-(IV), the therapeutic agent is selected from a small molecule, a peptide, a protein, a nucleic acid, a gene editing reagent, and a targeting molecule.

In some embodiments of the composition comprising a compound of any one of Formulas (I)-(IV), the therapeutic agent is a small molecule selected from folic acid, thiamine, dimercaptosuccinic acid, and the like; a protein selected from BSA, transferrin, antibodies, lectins, cytokines, fibrinogen, thrombin, and the like; or a polysaccharide selected from hyaluronic acid, chitosan, dextran, oligosaccharides, heparin, and a polyunsaturated fatty acid.

In some embodiments of the composition comprising a compound of any one of Formulas (I)-(IV), the therapeutic agent is targeting molecule that is a surface targeting modifier.

In some embodiments of the composition comprising a compound of any one of Formulas (I)-(IV), the surface targeting modifier is selected from RGD, c(CMGRC), PHSRN (SEQ ID NO:5), LHRD, antigenic peptides, internalization peptides, cell penetrating peptides, VP22, RPRAPARSASRPRRPVE (SEQ ID NO:6), sC18, GLRKRLRKFRNKIKEK (SEQ ID NO: 7), Pept1, PLILLRLLRGQF (SEQ ID NO: 8), Transferrin, OX26, CAQK, Lactoferrin, F3, KDEPQRRSARLSAKPAPPK-PEPKPKKAPAKK (SEQ ID NO:9), Lyp-1, CGNKRTRGC (SEQ ID NO:10), CREKA (SEQ ID NO: 11), Bld-3, CSNRDARRC (SEQ ID NO:12), AHNP, YCDGFYA-CYMDV (SEQ ID NO:13), SP204, KQFSALPFNFYT peptide (SEQ ID NO: 14), EGF, VEGF, LFA-1, Apolipoprotein AI, Infarcted cardiac tissue targeting, SP204, PLGLAGGWGERDGS (SEQ ID NO 15), GGGGY-DRVTIHPF (SEQ ID NO: 16), VCAM-1, VHSPNKK (SEQ ID NO: 17), VHPKQHR (SEQ ID NO: 18), VLTTGLPAL-ISWIKRKRQQ (SEQ ID NO: 19), NNSKSHT (SEQ ID NO: 20), VHPKQHRAEEEAK (SEQ ID NO: 21), C*NNSKSHTC*C (SEQ ID NO: 22), VHPK, VHPKQHRGGSKGC(SEQ ID NO: 23), VHSPNKK peptide (SEQ ID NO: 24), Ab(M/K2.7), Ab(429), antibodies, nanobodies, PECAM-1, Ab, ICAM-1, LFA-1 integrin, and Ab(R6.5).

In some embodiments of the composition comprising a compound of any one of Formulas (I)-(IV), the therapeutic agent is targeting molecule that is a membrane dipeptidase targeting molecule. For example, the membrane dipeptidase targeting molecule may be GFE or CGFECVRQCPERC (SEQ ID NO: 26).

In some embodiments of the composition comprising a compound of any one of Formulas (I)-(IV), the therapeutic agent is targeting molecule that is an endoplasmic reticulum (ER) targeting molecule. For example, the endoplasmic reticulum (ER) targeting molecule may be selected from KDEL, SEKDEL (SEQ ID NO:27), Eriss, and MRYMILGLLALAAVCSA (SEQ ID NO:28).

In some embodiments of the composition comprising a compound of any one of Formulas (I)-(IV), the therapeutic agent is targeting molecule that is a mitochondrial membrane targeting molecule. For example, the mitochondrial membrane targeting molecule may be selected from RGD-4C-GG-D (KLAKLAK) (SEQ ID NO:29), D-Arg-Dmt-Lys-Phe-NH₂, Phe-D-Arg-Phe-Lys-NH₂, Phe-D-Arg-DmtOrn-Phe-NH₂ (SEQ ID NO:30), D-Arg-(2'6'-dimethylTyr)-Lys-Phe-NH2 (SEQ ID NO:31), (1,7-bis-4-hydroxy-3-methoxyphenyl-1,6-heptadiene-3,5-dione)-triphenyl-phospine, 1,5-dioctadecyl-Lglutamyl 2-histidly-hexahydrobenzoic acid-SPC-L, MSVLTPLLLRGLTGSARRLPVPRAKIHWLC (SEQ ID NO:32), GKRK, and D[KLAKLAK]2 (SEQ ID NO:33).

In some embodiments of the composition comprising a compound of any one of Formulas (I)-(IV), wherein the therapeutic agent is targeting molecule that is a nucleus targeting molecule. For example, the nucleus targeting molecule may be selected from KKKRKV (SEQ ID NO:34), KRPAATKKAGQAKKKKL (SEQ ID NO:35), HIV1 TAT, GRKKRRQRRRPQ (SEQ ID NO:36), R8, RRRRRRRR (SEQ ID NO:37), Penetratin, RQIKIWFQNRRMKWKK (SEQ ID NO:38), HA2 peptide, GDIMGEWGNEIFGA-IAAGFLG (SEQ ID NO:39), GALA, WEAALAEALAEA-LAEHLAEALAEALEALAA (SEQ ID NO:40), Pas, FFLIPKG (SEQ ID NO:41), THRPPMWSPWVWP (SEQ ID NO:42), angiopep-2, TFFYGGSRGKRNNFKTEEY (SEQ ID NO:43), Glutathione, (γE)CG, CDX, FKESWREARGTRIERG (SEQ ID NO:44), Chlorotoxin, MCMPCFTTDHQ-MARKCDDCCGGKGRGKCYGPQCLCR (SEQ ID NO:45), MiniAP-4, c(DLATEPAL[Dap]) (SEQ ID NO:46), g7, GFTGFLS(Glucose) (SEQ ID NO:48), RV29, YTIWMPENPRPGTPCDIFTNSRGKRASNG (SEQ ID NO:48), iRGD, CRGDKRGPDEC (SEQ ID NO:49), IL-13p, TAMRAVDKLLLHLKKLFREGQFNRNFESIII-CRDRT (SEQ ID NO:50), CGEMGWVRC (SEQ ID NO:51), Lyp-1, c(CGNKRTRGC) (SEQ ID NO:52), DOPAC-MYIEALDKYAC-COOH (SEQ ID NO:53), and Pro-Lys-Lys-Lys-Arg-Lys-Val, Ala-Ala-Phe-Glu-Asp-Leu-Arg-Val-Leu-Ser, Lys-Arg-Pro-Ala-Ala-Thr-LysLys-Arg-Gly-Qln-Arg-Lys-Lys-Lys-Lys (SEQ ID NO:54).

In some embodiments, disclosed herein is a composition comprising a compound of Formula (V):

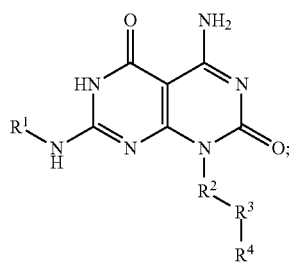

(V)

or a pharmaceutically acceptable salt thereof, wherein:
$R^1$ is H or $CH_3$;
$R^2$ is $(CH_2)_j$, $(CH_2CH_2O)_k$, or $(CH_2CH_2NH)_m$;
j, k, and m are each independently 0-200;
$R^3$ is absent or α-amino acid, β-amino acid, α-polypeptide, or β-polypeptide; and
$R^4$ is absent or a coating material.

In some embodiments, disclosed herein is a composition comprising a compound of Formula (VI):

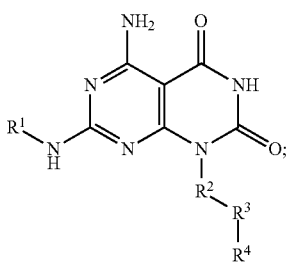

(VI)

or a pharmaceutically acceptable salt thereof, wherein:
$R^1$ is H or $CH_3$;
$R^2$ is $(CH_2)_j$, $(CH_2CH_2O)_k$, or $(CH_2CH_2NH)_m$;
j, k, and m are each independently 0-200;
$R^3$ is absent or α-amino acid, β-amino acid, α-polypeptide, or β-polypeptide; and
$R^4$ is absent or a coating material.

In some embodiments, disclosed herein is a composition comprising a compound of Formula (VII):

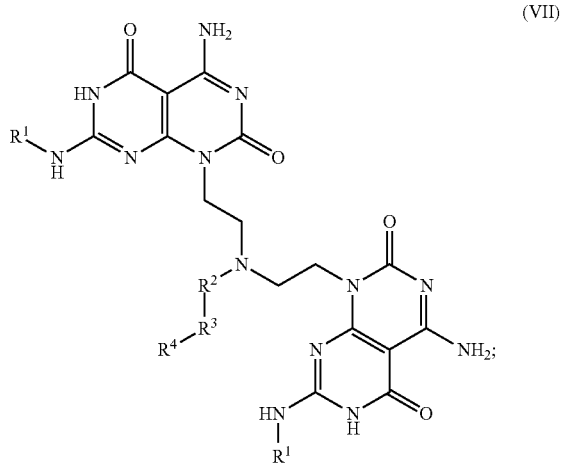

(VII)

or a pharmaceutically acceptable salt thereof, wherein:
$R^1$ is H or $CH_3$;
$R^2$ is $(CH_2)_j$, $(CH_2CH_2O)_k$, or $(CH_2CH_2NH)_m$;
j, k, and m are each independently 0-200;
$R^3$ is absent or α-amino acid, β-amino acid, α-polypeptide, or β-polypeptide; and
$R^4$ is absent or a coating material.

In some embodiments, disclosed herein is a composition comprising a compound of Formula (VIII):

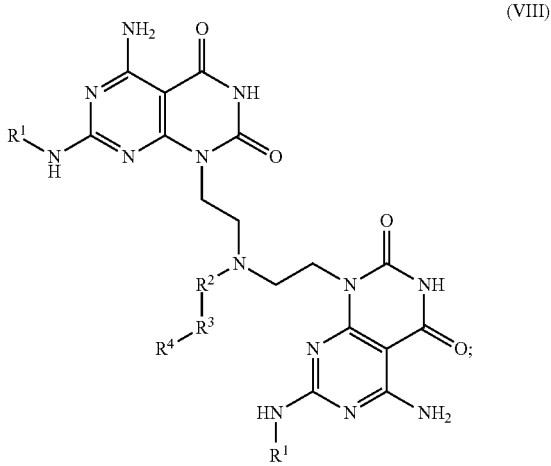

(VIII)

or a pharmaceutically acceptable salt thereof, wherein:
$R^1$ is H or $CH_3$;
$R^2$ is $(CH_2)_j$, $(CH_2CH_2O)_k$, or $(CH_2CH_2NH)_m$;
j, k, and m are each independently 0-200;
$R^3$ is absent or α-amino acid, β-amino acid, α-polypeptide, or β-polypeptide; and
$R^4$ is absent or a coating material.

In some embodiments of the composition comprising any one of compounds of Formulas (V)-(VIII), $R^4$ is absent.

In some embodiments of the composition comprising any one of compounds of Formulas (V)-(VIII), $R^4$ is a coating material.

In some embodiments of the composition comprising any one of compounds of Formulas (V)-(VIII), the coating material is selected from chitosan, polyethylene glycol, hyaluronic acid, poloxamer, polyvinyl alcohol, polysaccharides, neutral or negatively charged poly(amino acids); CALNN (SEQ ID NO:55), CCVVT (SEQ ID NO:56), CLPFFD (SEQ ID NO:57), phytochelatin, (γE)C(γE)C(γE)CG, GCK15, GCGGCGGKGGCGGCG (SEQ ID NO:58), and Hexahistidine (HHHHHH) (SEQ ID NO:59).

In some embodiments of the composition comprising any one of compounds of Formulas (I)-(VIII), the composition comprises 0.1% to 99.9% of one or more compounds of Formulas (I)-(VIII).

In some embodiments of the composition comprising any one of compounds of Formulas (I)-(VIII), the composition comprises a concentration of 1 µg/mL to 1 g/mL of one or more compounds of Formulas (I)-(VIII).

In some embodiments of the composition comprising any one of compounds of Formulas (I)-(VIII), the composition has a pH of about 1 to about 10.

Also disclosed herein are methods of treating a viral infection comprising administering a composition comprising any one or more of compounds of Formulas (I)-(VIII) to a subject in need thereof. In some embodiments, the viral infection is COVID-19.

BRIEF DESCRIPTION OF THE FIGURES

The patent or application file contains at least one drawing executed in color. Copies of this patent or patent application publication with color drawings will be provided by the Office upon receipt and payment of the necessary fee.

FIGS. 2a-f show characterization of an exemplary JBNP.

FIGS. 3a-3b show an exemplary JBNP delivered into cells.

FIGS. 4a-4c show endosomal escape of an exemplary JBNP in cells.

DETAILED DESCRIPTION

Figure 1A:
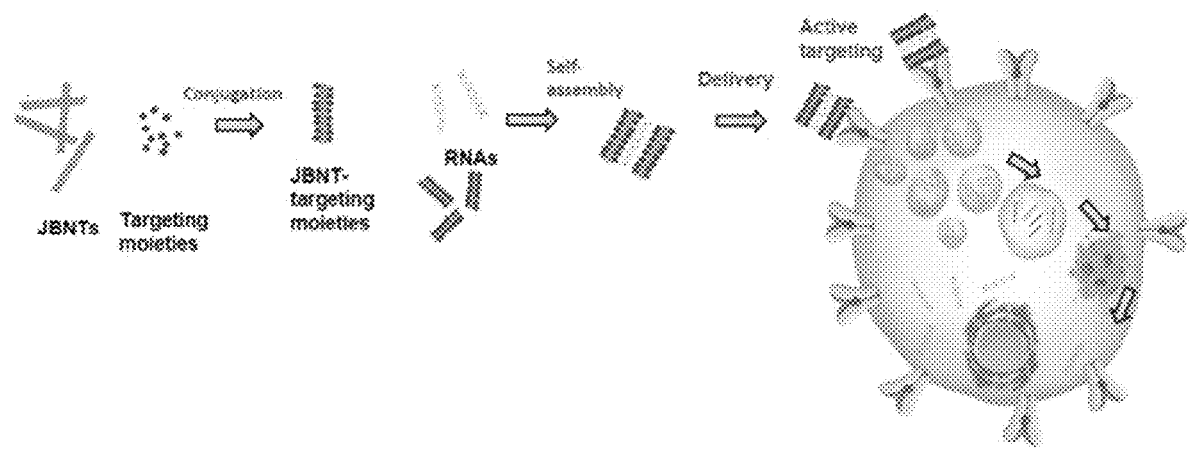
FIG. 1a shows a schematic drawing of an exemplary JBNP and uptake.
Figure 1B:
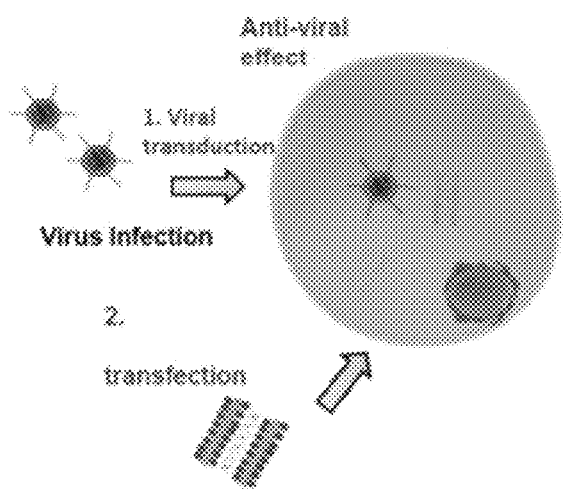
FIG. 1b shows schematic drawing of an exemplary antiviral experiment using JBNPs.

To achieve active cell targeting, surface modification of a JBNP with various targeting moieties (e.g., small molecules, amphiphilic polymers, aptamers, proteins, peptides, carbohydrates, antibodies, lectin, and the like) can facilitate specific and selective uptake pathways by targeting specific receptors on the surface of various cells (FIG. 1a). For anti-viral treatment, different kinds of recognition molecules that can bind specifically to infected cells have been attached on the JBNPs (FIG. 1b).

A range of biomoieties can be conjugated to the JBNPs including ligand molecules such as folic acid, thiamine, dimercaptosuccinic acid, and the like; proteins including BSA, transferrin, antibodies, lectins, cytokines, fibrinogen, thrombin, and the like; polysaccharides including hyaluoronic acid, chitosan, dextran, oligosaccharides, heparin, and the like; and polyunsaturated fatty acids including palmitic acid, phospholipids, and the like, can be conjugated to the JBNP.

Surface targeting modifiers specific for infected cells also include peptides. Peptide sequences are coupled to JBNTs and are able to target the cells and transport them across the plasma membrane. Peptide include RGD, LHRD, antigenic peptides, internalization peptides, cell-penetrating peptides, and the like.

For COVID-19 treatment, an aptamer targeting SARS-CoV-2 receptor-binding domain and ligands targeting angiotensin-converting enzyme II (ACE2) can be used.

For HIV treatment, JBNPs can be conjugated with transferrin (Tf). For hepatitis B virus (HBV) treatment, a proposed design is that the hepatitis B surface antigen (HBsAg) surface-modification of a JBNP can deliver siRNA to target to hepatocytes.

For vaccines, JBNPs can be modified to carry antigens or epitomes to target antigen-presenting cells, such as cetyltrimethylammonium bromide (CTAB), poly(diallydimethylammonium chloride) (PDDAC), and polyethyleneimine (PEI), etc. The JBNPs can also be functionalized with surface hydroxyl groups and CpG peptides.

Herein, novel delivery NPs were developed based on JBNTs with excellent endosomal escape and low cytotoxicity. The nanoparticles are referred to herein NPs or JBNPs.

Definitions

Throughout the present specification and the accompanying claims the words "comprise," "include," and "have" and variations thereof such as "comprises," "comprising," "includes," "including," "has," and "having" are to be interpreted inclusively. That is, these words are intended to convey the possible inclusion of other elements or integers not specifically recited, where the context allows. No language in the specification should be construed as indicating any non-claimed element essential to the practice of the invention.

The terms "a," "an," and "the" and similar referents used in the context of describing the invention (especially in the context of the following claims) are to be construed to cover both the singular and the plural, unless otherwise indicated herein or clearly contradicted by context.

The terms first, second, etc. as used herein are not meant to denote any particular ordering, but simply for convenience to denote a plurality of, for example, layers.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximately") one particular value, and/or to "about" (or "approximately") another particular value. When such a range is expressed, another embodiment includes from the one particular value and/or to the other particular value. Similarly, when values are expressed as approximations, by use of the antecedent "about" or "approximately" it will be understood that the particular value forms another embodiment. It will be further understood that the endpoints of each of the ranges are disclosed both in relation to the other endpoint, and independently of the other endpoint.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g., "such as") provided herein is intended merely to better illuminate the invention and does not pose a limitation on the scope of the invention otherwise claimed.

Units, prefixes, and symbols are denoted in their Systeme International de Unites (SI) accepted form.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within +10% or 5% of the stated value.

As used herein, the term "administering" means the actual physical introduction of a composition into or onto (as appropriate) a host or cell. Any and all methods of introducing the composition into the host or cell are contemplated according to the invention; the method is not dependent on any particular means of introduction and is not to be so construed. Means of introduction are well-known to those skilled in the art, and also are exemplified herein.

As used herein, "optional" or "optionally" means that the subsequently described event or circumstance may or may not occur, and that the description includes instances where said event or circumstance occurs and instances where it does not.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the U.S. Pharmacopeia or other generally recognized pharmacopeia for use in animals, and more particularly in humans.

As used herein, the terms "treat," "treating," and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms also encompass therapy and cure. Treatment means any way the symptoms of a pathological condition, disorder, or disease are ameliorated or otherwise beneficially altered. Preferably, the subject in need of such treatment is a mammal, preferably a human.

Chemical Definitions

The term "amino acid" refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes without limitation, α-amino acids, natural amino acids, non-natural amino acids, and amino acid analogs.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive (10%) neutral (90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" are glycine, alanine, proline, and analogs thereof "Large hydrophobic amino acids" are valine, leucine, isoleucine, phenylalanine, methionine, tryptophan, and analogs thereof. "Polar amino acids" are serine, threonine, asparagine, glutamine, cysteine, tyrosine, and analogs thereof. "Charged amino acids" are lysine, arginine, histidine, aspartate, glutamate, and analogs thereof.

The term "amino acid analog" refers to a molecule which is structurally similar to an amino acid and that can be substituted for an amino acid in the formation of a peptidomimetic macrocycle. Amino acid analogs include, without limitation, β-amino acids, and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid that is not one of the twenty amino acids commonly found in peptides synthesized in nature, and known by the one letter abbreviations A, R, N, C, D, Q, E, G, H, I, L, K, M, F, P, S, T, W, Y and V. Non-natural amino acids or amino acid analogs include, without limitation, structures according to the following:

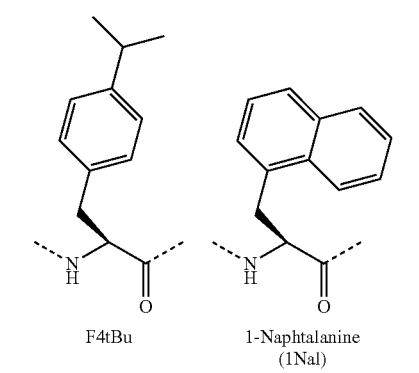

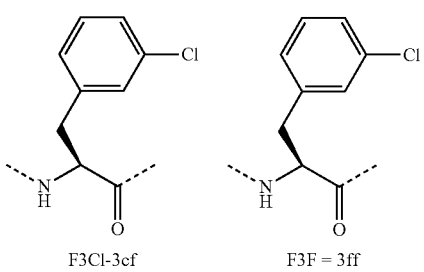

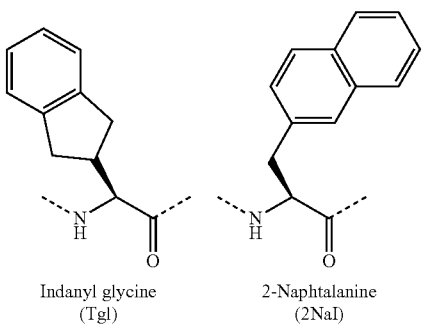

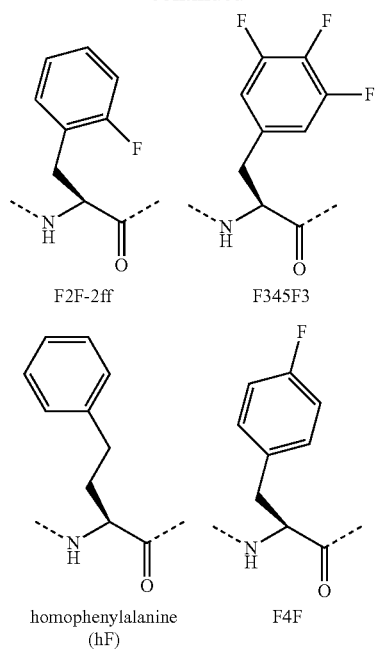

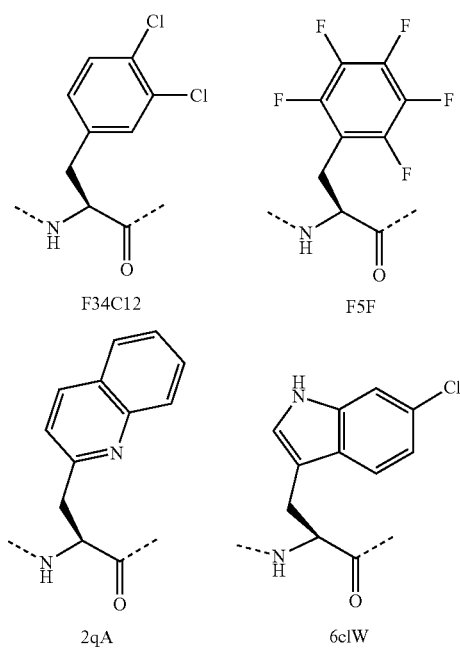

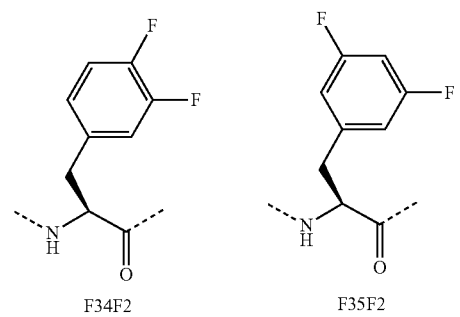

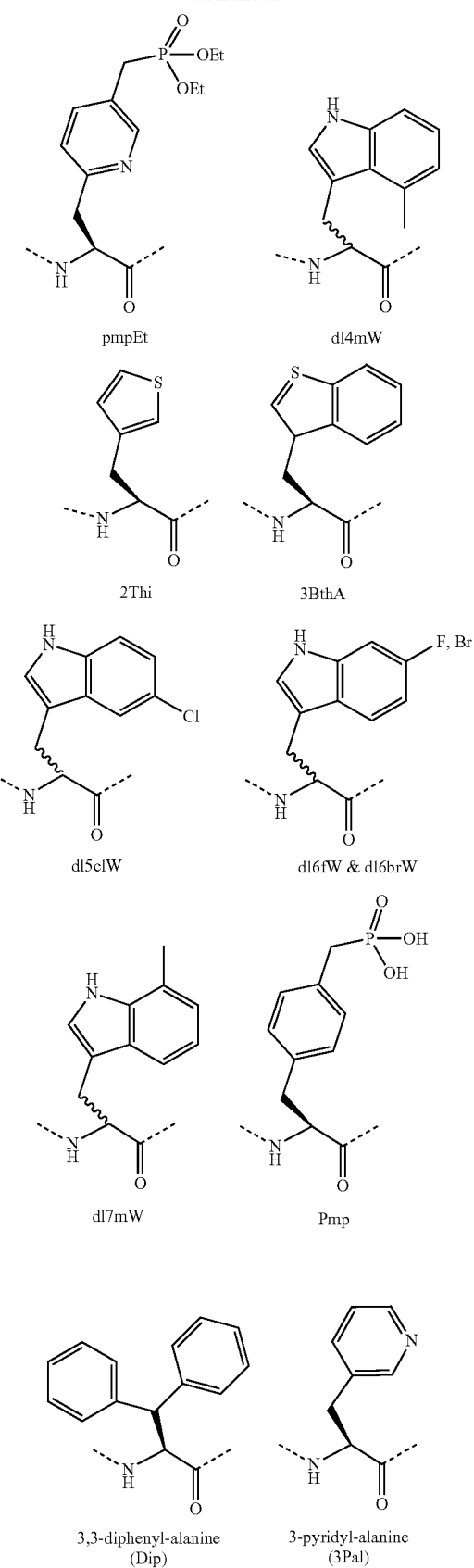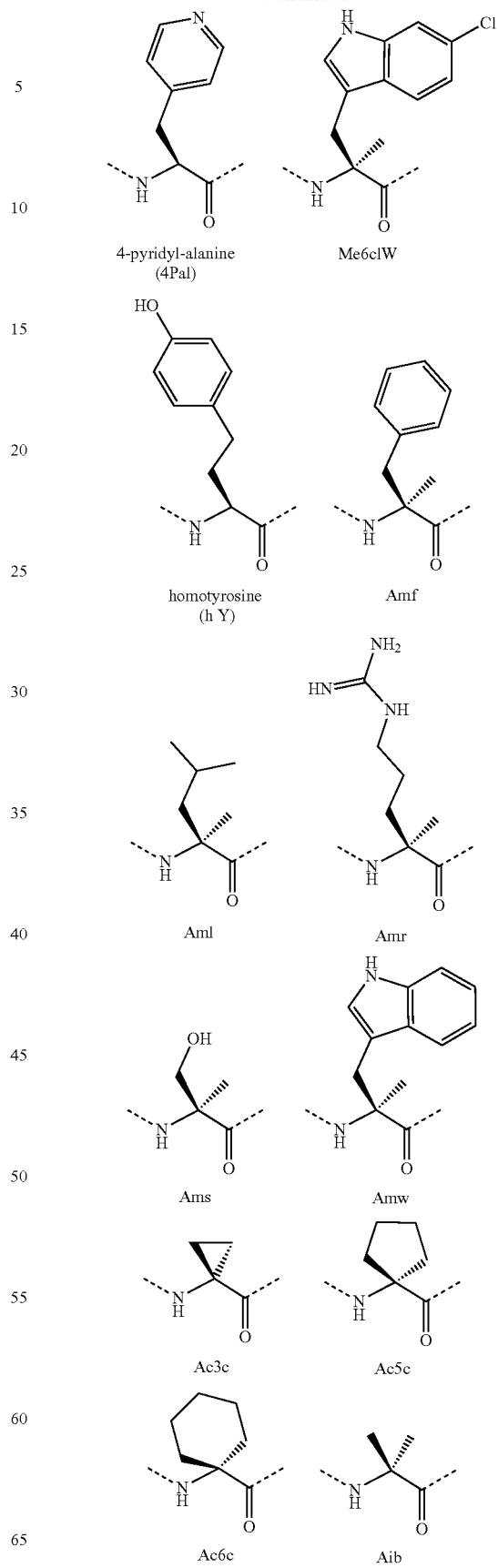

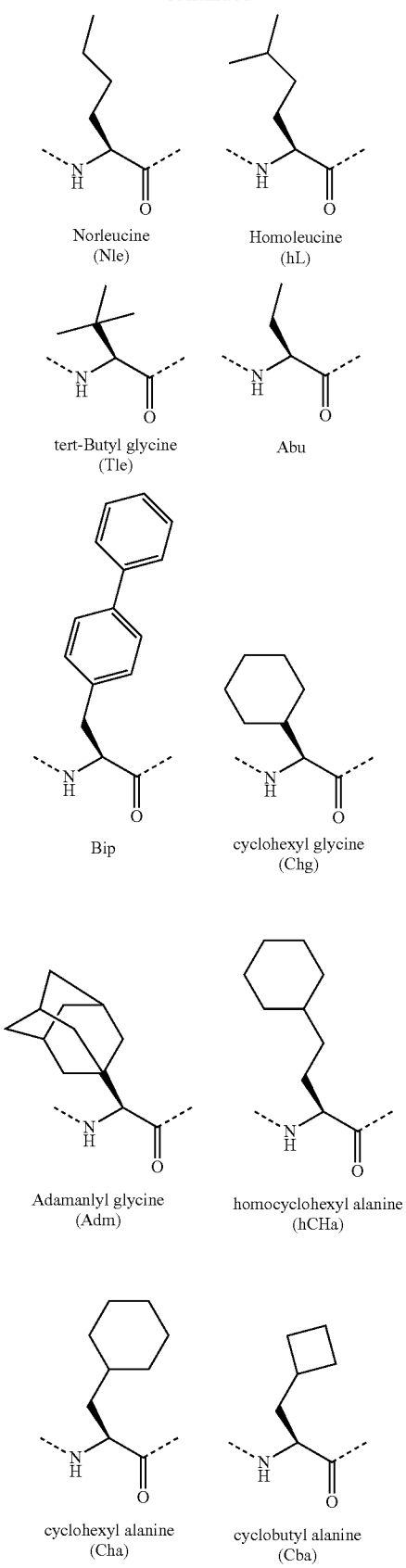
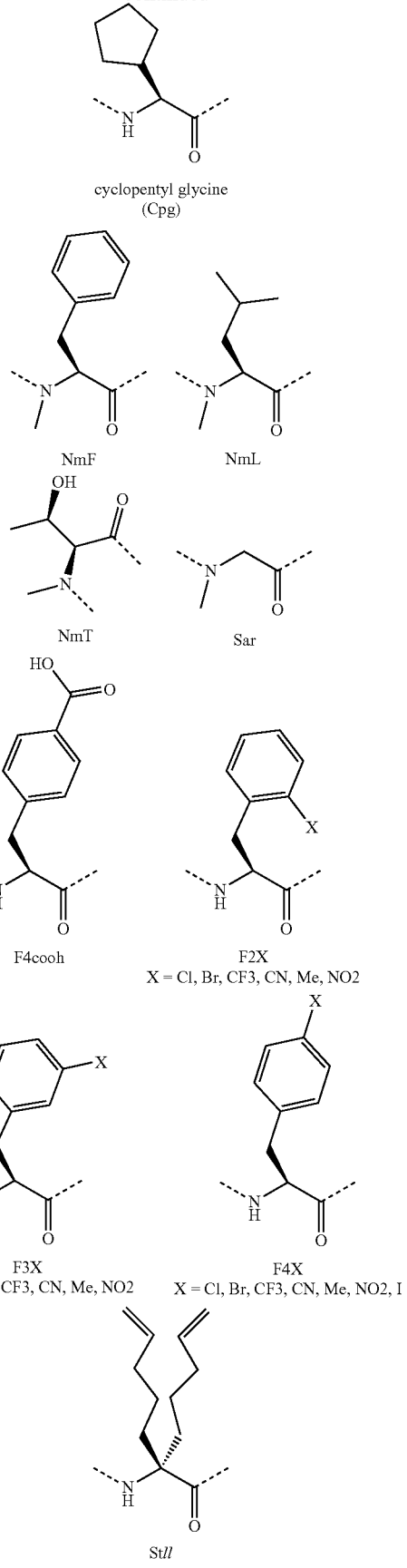

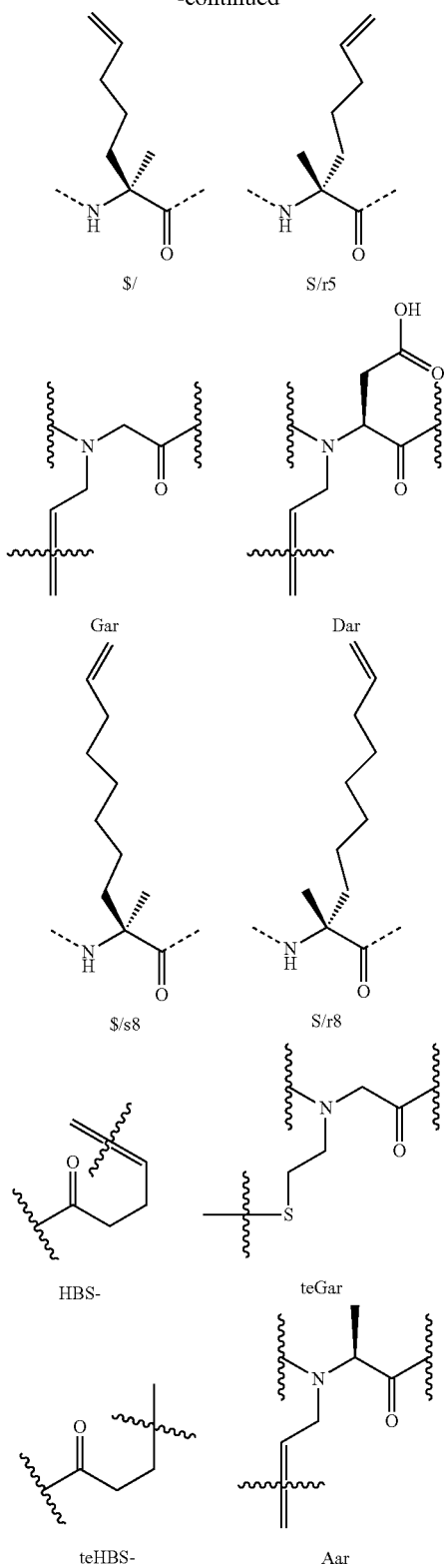

acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl)-butyric acid; (S)-3-amino-4-(4-cyanophenyl)-butyric acid; (S)-3-amino-4-(4-fluorophenyl)-butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-

Amino acid analogs include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; 1-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; 1-chloro-L-alanine; 1-cyano-L-alanin; 3-cyclohexyl-D-alanine; 3-cyclohexyl-L-alanine; 3-cyclopenten-1-yl-alanine; 3-cyclopentyl-alanine; 3-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH·dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH·dicyclohexylammonium salt; cyclopentyl-Gly-OH·dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine.dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-β-(dimethylamino)-propionic acid; L-α,β-diaminopropionic acid; L-α-aminobutyric acid; L-α-t-butylglycine; L-β-thienyl)glycine; L-2-amino-O-(dimethylamino)-propionic acid; L-2-aminocaproic acid dicyclohexyl-ammonium salt; L-2-indanylglycine; L-allylglycine·dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)₂-OH; Lys(N₃)—OH; Nδ-benzyloxycarbonyl-L-omithine; Nω-nitro-D-arginine; Nω-nitro-L-arginine; α-methyl-omithine; 2,6-diaminoheptanedioic acid; L-omithine; (Nδ-1-(4,4-dimethyl-2,6-dioxo-cyclohex-1-ylidene)ethyl)-D-omithine; (Nδ-1-(4,4-dimethyl-2,6-dioxo-cyclohex-1-ylidene)ethyl)-L-omithine; (Nδ-4-methyltrityl)-D-omithine; (Nδ-4-methyltrityl)-L-omithine; D-omithine; L-omithine; Arg(Me)(Pbf)-OH; Arg(Me)₂-OH (asymmetrical); Arg(Me)2-OH (symmetrical); Lys(ivDde)-OH; Lys(Me)2-OH·HCl; Lys(Me3)-OH chloride; Nω-nitro-D-arginine; and Nω-nitro-L-arginine.

Amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogs include analogs of phenylalanine and tyrosine. Examples of amino acid analogs of phenylalanine and tyrosine include 3-methyl-phenylalanine, 3-hydroxy-phenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L- phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; γ-benzyloxy-tryptophan; γ-bromo-tryptophan; γ-methyl-tryptophan; D-1,2,3,4-tetrahydro-norharman-3-carboxylic acid; 6-methoxy-1,2,3,4-tetrahydronorharman-1-carboxylic acid; γ-azatryptophan; L-1,2,3,4-tetrahydro-norharman-3-carboxylic acid; 5-methoxy-2-methyl-tryptophan; and 6-chloro-L-tryptophan.

In some embodiments, amino acid analogs are racemic. In some embodiments, the D isomer of the amino acid analog is used. In some embodiments, the L isomer of the amino acid analog is used. In other embodiments, the amino acid analog comprises chiral centers that are in the R or S configuration. In still other embodiments, the amino group(s) of a β-amino acid analog is substituted with a protecting group, e.g., tert-butyloxycarbonyl (BOC group), 9-fluorenylmethyloxycarbonyl (FMOC), tosyl, and the like. In yet other embodiments, the carboxylic acid functional group of a β-amino acid analog is protected, e.g., as its ester derivative. In some embodiments the salt of the amino acid analog is used.

A "non-essential" amino acid residue is a residue that can be altered from the wild-type sequence of a polypeptide without abolishing or substantially abolishing its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions are substitutions based on isosteric considerations (e.g. norleucine for methionine) or other properties (e.g., 2-thienylalanine for phenylalanine).

The term "polypeptide" refers to a linear organic polymer consisting of a large number of amino-acid residues bonded together in a chain, forming part of (or the whole of) a protein molecule.

The term "α-polypeptide" refers to are polypeptides derived from α-amino acids.

The term "β-polypeptide" refers to are polypeptides derived from β-amino acids.

The term "aliphatic" or "aliphatic group" refers to a hydrocarbon moiety that may be straight-chain (i.e., unbranched), branched, or cyclic (including fused, bridging, and spiro-fused polycyclic) and may be completely saturated or may contain one or more units of unsaturation. Suitable aliphatic groups include, but are not limited to, linear or branched, alkyl, alkenyl, and alkynyl groups, and hybrids thereof. As used herein the terms "aliphatic" or "aliphatic group", also encompass partially substituted analogs of these moieties where at least one of the hydrogen atoms of the aliphatic group is replaced by an atom that is not carbon or hydrogen.

The term "linker" refers to a chemical group that connects one or more other chemical groups via at least one covalent bond.

While the invention has been described with reference to an exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiments disclosed as the best mode contemplated for carrying out this invention, but that the invention will include all embodiments falling within the scope of the appended claims. Any combination of the described elements in all possible variations thereof is encompassed by the invention unless otherwise indicated herein or otherwise clearly contradicted by context.

Janus Base Nanotubes

A self-assembled nanomaterials of the present invention comprise Janus base nanotubes.

In some embodiments, the Janus base nanotube comprises a compound of Formula (I):

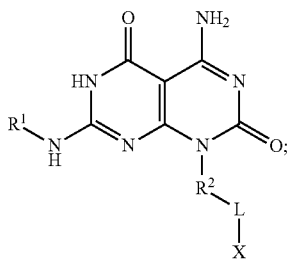

(I)

or a pharmaceutically acceptable salt thereof, wherein:
$R^1$ is H or $CH_3$; $R^2$ is $(CH_2)_j$, $(CH_2CH_2O)_k$ or $(CH_2CH_2NH)_m$;
j, k, and m are each independently 0-200;
L is absent or a linker group; and
X is a therapeutic agent.

In some embodiments, the Janus base nanotube comprises a compound of Formula (II):

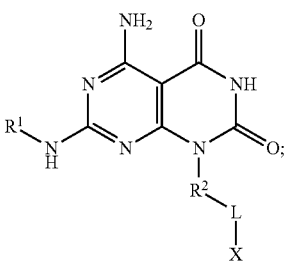

(II)

or a pharmaceutically acceptable salt thereof, wherein:
$R^1$ is H or $CH_3$; $R^2$ is $(CH_2)_j$, $(CH_2CH_2O)_k$ or $(CH_2CH_2NH)_m$;
j, k, and m are each independently 0-200;
L is absent or a linker group; and
X is a therapeutic agent.

In some embodiments, the Janus base nanotube comprises a compound of Formula (III):

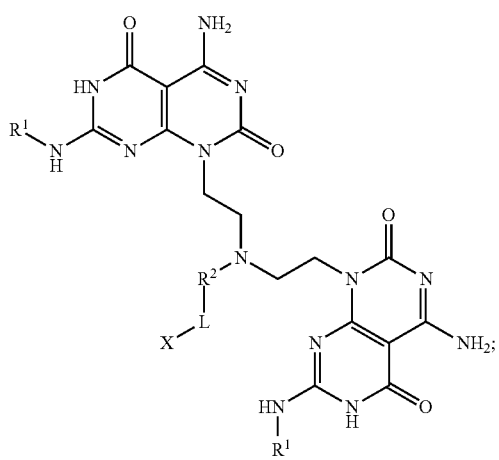

(III)

or a pharmaceutically acceptable salt thereof, wherein:
$R^1$ is H or $CH_3$; $R^2$ is from $(CH_2)_j$, $(CH_2CH_2O)_k$ or $(CH_2CH_2NH)_m$;

j, k, and m are each independently 0-200;
L is absent or a linker group; and
X is a therapeutic agent.

In some embodiments, the Janus base nanotube comprises a compound of Formula (IV):

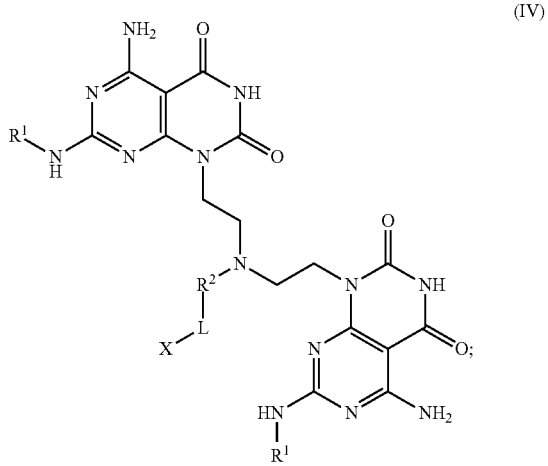

(IV)

or a pharmaceutically acceptable salt thereof, wherein:
$R^1$ is H or $CH_3$;
$R^2$ is $(CH_2)_j$, $(CH_2CH_2O)_k$, or $(CH_2CH_2NH)_m$;
j, k, and m are each independently 0-200;
L is absent or a linker group; and
X is a therapeutic agent.

Exemplary linker groups include:
(1) acid cleavable linkages such as, for example, N-acyl hydrazone, carbonate, and ester;
(2) reducible disulfide linkages such as, for example, N-succinimidyl-4-(2-pyridyldithio)pentanoate (SPP) and N-succinimidyl-4-(2-pyridyldithio)butyrate (SPDB), 4-(4'-acetylphenoxy)butanoic acid (AcBut) linkers, dipeptide Val-Cit and Phe-Lys type linkers, α-methyl substitution on disulfide linker, two-methyl groups on disulfide linker, engineered cysteine residue, and maytansinoid thiols; and
(3) stimuli linkers such as, for example, trans-cyclooctene linker, thioether-containing linker, enzyme cleavable linkers (GPLGOAGQ (SEQ ID NO:1), GDE-VEAPKGC (SEQ ID NO: 2), citrulline-valine, Glycosidase-cleavable linker, β-glucuronidase-cleavable linker, β-Galactosidase-cleavable linker, phosphatase cleavable linker, pyrophosphate-containing linker, dipeptide-containing linkers, Gly-Phe-LeuGly (SEQ ID NO:3), Ala-Leu-Ala-Leu, Phe-Lys-PABC (para-aminobenzyl carbamate) (SEQ ID NO:4), Val-Cit-PABC containing linker, Glu-Val-Cit-containing linker, and Val-Ala containing linker.

Exemplary therapeutic agents include small molecules, peptides, proteins, nucleic acids, gene editing reagents, and targeting molecules.

Exemplary small molecules include folic acid, thiamine, dimercaptosuccinic acid, and the like; proteins include BSA, transferrin, antibodies, lectins, cytokines, fibrinogen, thrombin, and the like; polysaccharides include hyaluronic acid, chitosan, dextran, oligosaccharides, heparin, and the like; and polyunsaturated fatty acids include palmitic acid, phospholipids, and the like, that can be conjugated to the NPs.

Exemplary surface targeting modifiers include those that are specific for infected cells/tissues such as, for example RGD, c(CMGRC), PHSRN (SEQ ID NO:5), LHRD, antigenic peptides, internalization peptides, cell penetrating peptides, VP22, RPRAPARSASRPRRPVE (SEQ ID NO:6), sC18, GLRKRLRKFRNKIKEK (SEQ ID NO:7), Pept1, PLILLRLLRGQF (SEQ ID NO:8) and the like. BBB penetration agents include transferrin, OX26, CAQK and lactoferrin. Tumor targeting gents include F3, KDEPQRR-SARLSAKPAPPKPEPKPKKAPAKK (SEQ ID NO:9), Lyp-1, CGNKRTRGC (SEQ ID NO:10), CREKA (SEQ ID NO: 11), Bld-3, CSNRDARRC (SEQ ID NO:12), AHNP, YCDGFYACYMDV (SEQ ID NO:13), SP204, KQFSALPFNFYT peptide (SEQ ID NO:14). Tumour targeting proteins include transferrin, EGF, VEGF, LFA-1, Apolipoprotein AI. Infarcted cardiac tissue targeting, SP204, PLGLAGGWGERDGS (SEQ ID NO:15), GGGGY-DRVTIHPF (SEQ ID NO:16). Atherosclerotic-related disease targeting agents include VCAM-1, VHSPNKK (SEQ ID NO: 17), VHPKQHR (SEQ ID NO: 18), VLTTGLPAL-ISWIKRKRQQ (SEQ ID NO: 19), NNSKSHT (SEQ ID NO:20), VHPKQHRAEEAK (SEQ ID NO:21), C*NNSKSHTC*C (SEQ ID NO:22), VHPK, VHPKQHRGGSKGC (SEQ ID NO:23), VHSPNKK peptide (SEQ ID NO:24), Ab(M/K2.7), Ab(429), antibodies, nanobodies, PECAM-1, Ab, ICAM-1, LFA-1 Integrin, Ab(R6.5). White fat targeting agents include SP204, CKG-GRAKDC (SEQ ID NO:25). Alveoli targeting proteins include WGA. Intestinal targeting proteins include UEA-1.

Other exemplary targeting molecules include membrane dipeptidase targeting molecules such as, for example, GFE and CGFECVRQCPERC (SEQ ID NO:26); endoplasmic reticulum (ER) targeting molecules such as, for example, KDEL peptide, SEKDEL (SEQ ID NO:27), Eriss, and MRYMILGLLALAAVCSA peptide (SEQ ID NO:28); mitochondrial membrane targeting molecules such as, for example, RGD-4C-GG-D (KLAKLAK)2,D-Arg-Dmt-Lys-Phe-NH2 (SEQ ID NO:29), Phe-D-Arg-Phe-Lys-NH2 (SEQ ID NO:30), D-Arg-DmtOrn-Phe-NH2,D-Arg-(2'6'-dimethylTyr)-Lys-Phe-NH2 (SEQ ID NO:31), (1,7-bis-4-hydroxy-3-methoxyphenyl-1,6-heptadiene-3,5-dione)-triphenyl-phospine, 1,5-dioctadecyl-Lglutamyl 2-histidly-hexahydrobenzoic acid-SPC-L, MSVLTPLLLRGLTGSARRLPVPRAKIHWLC (SEQ ID NO:32), GKRK, D[KLAKLAK]2 (SEQ ID NO:33); and nucleus targeting molecules such as, for example, KKKRKV (SEQ ID NO:34), KRPAATKKAGQAKKKKL (SEQ ID NO:35), HIV1 TAT, GRKKRRQRRRPQ (SEQ ID NO:36), R8, RRRRRRRR (SEQ ID NO:37), Penetratin, RQIKIWFQNRRMKWKK (SEQ ID NO:38), HA2 peptide, GDIMGEWGNEIFGAIAAGFLG (SEQ ID NO:39), GALA, WEAALAEALAEALAEHLAEALAEALEALAA (SEQ ID NO:40), Pas, FFLIPKG (SEQ ID NO:41), THRPPMWSPWVWP (SEQ ID NO:42), angiopep-2, TFFYGGSRGKRNNFKTEEY (SEQ ID NO:43), Glutathione, (γE)CG, CDX, FKESWREARGTRIERG (SEQ ID NO:44), Chlorotoxin, MCMPCFTTDHQ-MARKCDDCCGGKGRGKCYGPQCLCR (SEQ ID NO:45), MiniAP-4, c(DLATEPAL[Dap]) (SEQ ID NO:46), g7, GFTGFLS(Glucose) (SEQ ID NO:47), RV29, YTIWMPENPRPGTPCDIFTNSRGKRASNG (SEQ ID NO:48), iRGD, CRGDKRGPDEC (SEQ ID NO:49), IL-13p, TAMRAVDKLLLHLKKLFREGQFNRNFESIII-CRDRT (SEQ ID NO:50), CGEMGWVRC (SEQ ID NO:51), Lyp-1, c(CGNKRTRGC) (SEQ ID NO:52), DOPAC-MYIEALDKYAC-COOH (SEQ ID NO:53), Pro-Lys-Lys-Lys-Arg-Lys-Val, Ala-Ala-Phe-Glu-Asp-Leu-Arg-Val-Leu-Ser, Lys-Arg-Pro-Ala-Ala-Thr-LysLys-Arg-Gly-Qln-Arg-Lys-Lys-Lys-Lys (SEQ ID NO:54).

In some embodiments, the Janus base nanotube comprises a compound of Formula (V):

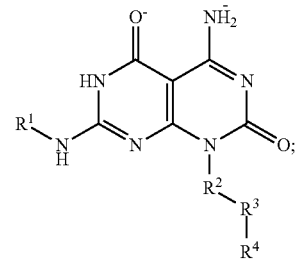

(V)

or a pharmaceutically acceptable salt thereof, wherein:

$R^1$ is H or $CH_3$;

$R^2$ is $(CH_2)_j$, $(CH_2CH_2O)_k$, or $(CH_2CH_2NH)_m$;

j, k, and m are each independently 0-200;

$R^3$ is absent or α-amino acid, β-amino acid, α-polypeptide, or β-polypeptide; and $R^4$ is absent or a coating material.

In some embodiments, the Janus base nanotube comprises a compound of Formula (VI):

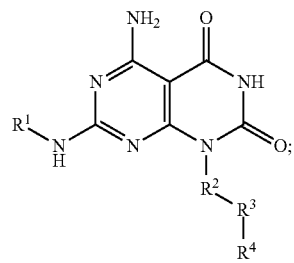

(VI)

or a pharmaceutically acceptable salt thereof, wherein:

$R^1$ is H or $CH_3$;

$R^2$ is $(CH_2)_j$, $(CH_2CH_2O)_k$, or $(CH_2CH_2NH)_m$;

j, k, and m are each independently 0-200;

$R^3$ is absent or α-amino acid, β-amino acid, α-polypeptide, or β-polypeptide; and $R^4$ is absent or a coating material.

In some embodiments, the Janus base nanotube comprises a compound of Formula (VII):

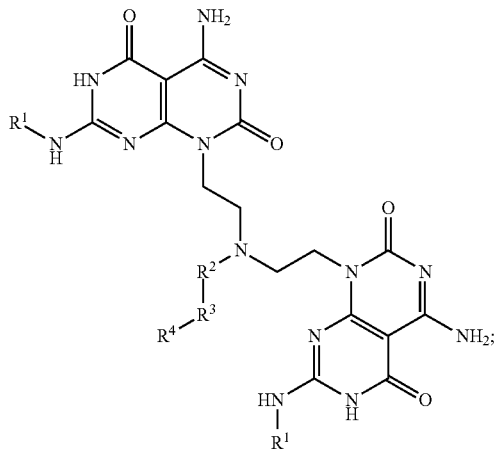

(VII)

or a pharmaceutically acceptable salt thereof, wherein:
R[1] is H or CH$_3$;
R[2] is (CH$_2$)$_j$, (CH$_2$CH$_2$O)$_k$, or (CH$_2$CH$_2$NH)$_m$;
j, k, and m are each independently 0-200;
R[3] is absent or α-amino acid, β-amino acid, α-polypeptide, or β-polypeptide; and
R[4] is absent or a coating material.

In some embodiments, the Janus base nanotube comprises a compound of Formula (VIII):

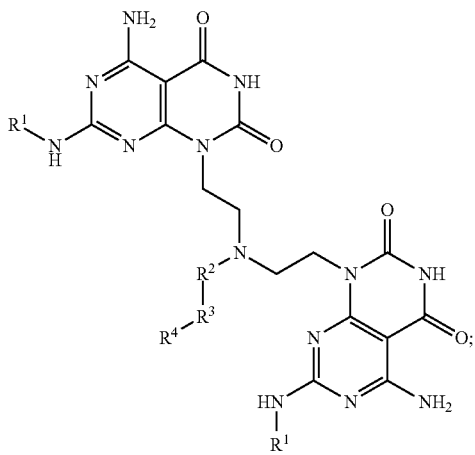

(VIII)

or a pharmaceutically acceptable salt thereof, wherein.
R[1] is H or CH$_3$;
R[2] is (CH$_2$)$_j$, (CH$_2$CH$_2$O)$_k$, or (CH$_2$CH$_2$NH)$_m$;
j, k, and m are each independently 0-200;
R[3] is absent or α-amino acid, β-amino acid, α-polypeptide, or β-polypeptide; and
R[4] is absent or a coating material.

Exemplary coating materials include chitosan, polyethylene glycol, hyaluronic acid, poloxamer, polyvinyl alcohol, polysaccharides and neutral or negatively charged poly (amino acids), CALNN (SEQ ID NO:55), CCVVT (SEQ ID NO:56), CLPFFD (SEQ ID NO:57), phytochelatin, (γE)C (γE)C(γE)CG, GCK15, GCGGCGGKGGCGGCG (SEQ ID NO:58), and hexahistidine (HHHHHH) (SEQ ID NO:59).

Compositions Comprising Janus Base Nanotubes

In some embodiments, disclosed herein are compositions comprising the JBNTs of the invention. In particular, such compositions comprise a JBNT comprising one or more compounds of any one of Formulas (I)-(VIII). In such compositions, the compounds of any one of Formulas (I)-(VIII) can be combined in any combination.

In some embodiments, the compositions of the invention comprise 0.1% to 99.9% of one or more compounds of Formulas (I)-(VIII). In some embodiments, the compositions of the invention comprise a concentration of 1 μg/mL to 1 g/mL of one or more compounds of Formulas (I)-(VIII).

In some embodiments, the composition has a pH of about 1 to about 10.

The compositions disclosed herein offer several advantages. Such advantages include, but are not limited to:

The materials have low cytotoxicity and low immunogenicity, which can minimize the side effects caused by the material itself when used for delivery of small molecules/proteins/nucleic acids/gene editing tools.

The materials stand out by improved endosomal escape leading to high efficacy.

The materials are conjugated with targeting moieties to achieve active cell targeting to specific targeting cell/tissues.

Co-assembly of different functional groups with different ranges of ratio can be designed for designed properties of the material.

The encapsulation of cargoes can be achieved either by covalent bonds or noncovalent bonds.

The materials can be linked with various linkers to achieve control release of the cargoes.

Advantageously, the compositions described herein combine advantages from lipid nanoparticles and cationic polymers for improved endosomal escape, high efficacy and low toxicity. The NPs can efficiently enter cells via macropinocytosis (the same mechanism as lipid nanoparticles), and can effectively escape from endosomes via the "proton sponge" effect (the same mechanism as cationic polymers). Therefore, the JBNPs can achieve excellent delivery of cargoes and have extremely low cytotoxicity for applications, such as antiviral therapy.

The compositions described herein enable delivery into different cell organelles with targeting molecules. To achieve the active cell targeting, surface modification of the NPs with various targeting moieties (small molecules, amphiphilic polymers, aptamers, proteins, peptides, carbohydrates, antibodies or lectin) can facilitate specific and selective uptake pathways by targeting specific receptors on the surface of various cells.

Co-assembly enables multiple functions with targeting molecules. Co-assembly of the different units with targeting moieties can be designed to have various properties such as increasing hydrophobicity, stability, and self-assembly. This is linked to the cellular delivery, including proton sponge effect, circulation time in vivo, passive or active targeting, subcellular targeting, improved cellular uptake, and enhanced endosomal escape.

The compositions also enable the possibility of covalent conjugation with cargos. Covalent cargoes involve chemically bonded tethers to the material and cargoes.

Conditional cleavage of the linker is also provided. A linkage molecule or linkage peptide can be conjugated to the materials for controlled release of cargoes after cellular delivery. Chemically cleavable linkers including acid cleavable, reducible disulfides and stimuli linker can be conjugated.

Co-assembly of different formulas can also be achieved.

Conjugation of coating materials can protect the delivery vehicle from specific/non-specific clearance of cells and organs.

Antiviral Therapy

The JBNPs disclosed herein can actively target infected cells or pre-deliver to cells to efficiently deliver siRNAs with significantly lower cytotoxicity than commonly used vectors such as lipid nanoparticles or cationic polymers. As a proof-of-concept, the JBNPs disclosed herein were demonstrated to effectively inhibit the viral gene better than lipofectamine with high biocompatibility. The JBNP platform may have benefits for effective anti-viral treatment and reducing the side-effects on patients.

For successful antiviral therapy, it is important to deliver therapeutics (such as siRNA) into the target cells (infected or pre-delivered) in a specific, effective, and safe manner.

Conventional delivery vectors such as lipid nanoparticles can deliver siRNAs, but are reported to have a low endosomal escape, which reduces antiviral efficacy. Moreover, the cationic lipid content tends to drive a pro-inflammatory phenotype. For instance, the Arbutus Biopharma Company's LNP shows an adverse toll-like receptor-mediated immune response in the later clinical trials. Cationic polymers can escape the endosome to efficiently deliver siRNAs, but show high cytotoxicity to the cells.

These limitations make it challenging to have a high efficacy of anti-viral therapy and have impeded translation of siRNA into clinics. Thus, siRNA carriers should be carefully tuned to allow binding, cell entry and endosome escape whilst minimizing toxicity. Moreover, immune stimulation of the carrier must be considered.

The JBNP platform stands out by combining advantages from lipid nanoparticles and cationic polymers for improved endosomal escape, high efficacy and low toxicity. This platform may serve as a highly commercially attractive for the antiviral applications in response to the COVID-19 pandemic.

The JBNTs disclosed herein can be used for RNAi therapy or anti-viral therapy. Further, the NP platform can be used for delivering anti-viral drugs or RNAs for management of patients with a viral disease such as, for example, COVID-19.

EXEMPLIFICATION

Example 1: Characterization of Compositions

Transmission Electron Microscope (TEM, FIG. 2a) was used to characterize the morphology of the JBNPs. Gel retardation assay (FIG. 2b) demonstrated the drug (siRNA) loading. Zeta potential (FIG. 2c) indicated the surface charge of the JBNPs. Ultraviolet-visible (UV-VIS) experiments (FIG. 2d) identified the incorporation between siRNA and JBNTs. Dynamic Light Scattering (DLS, FIG. 2e) showed the hydrodynamic sizes of the JBNPs in water. Acid-base titrations (FIG. 2f) determined the ability of the JBNPs to absorb protons, which is critical for endosomal escape.

FIG. 3a reveals the location of the green fluorescence labeled siRNA into cells. After 48 h, most of the observed siRNAs were found inside the cytosol. FIG. 3b shows the confocal microscopy Z-stacking image, which further supports the cytoplasmic localization of delivered payload. Overall, the NPs have successfully delivered siRNAs intracellularly. (3a) Confocal Laser Scanning Microscope (CLSM) images of siRNA-Alexa Fluor® 488 delivered to the I28/C2 cells via NP; stained with nuclei (blue) by DAPI, actin(red) by rhodamine phalloidin, and siRNA-Alexa Fluor® 488 (green) (3b) Z-stacks of the CLSM show the 3D view of NP delivery.

To correlate the buffering capacity of NPs and endosomal escape, bafilomycin A1 or chloroquine was treated to C28/I2 cells during transfection. FIG. 4s suggested that NPs can successfully escape the endosomal entrapment. FIG. 4b shows Colocalization analysis Pearson's R-value analysis of pre-treatment of bafilomycin A1 or chloroquine.

Figure 5A:
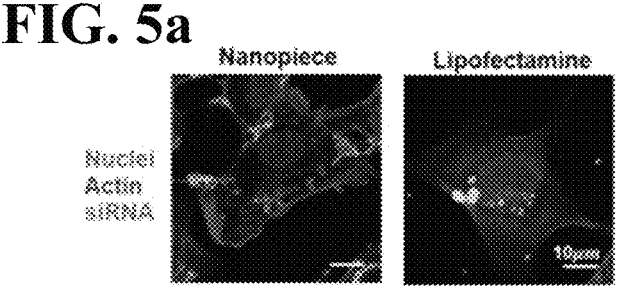
FIGS. 5a-5d show a comparison of the lipofectamine (Lipo) and an exemplary JBNP.
Figure 5B:
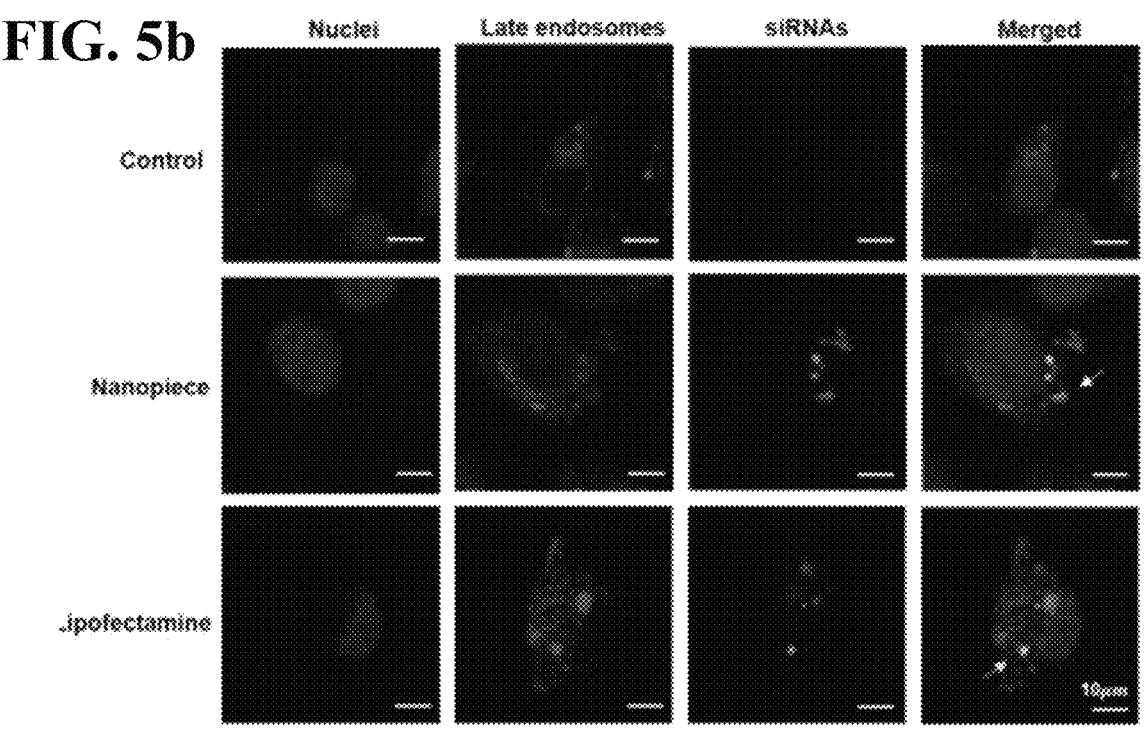
Figure 5C:
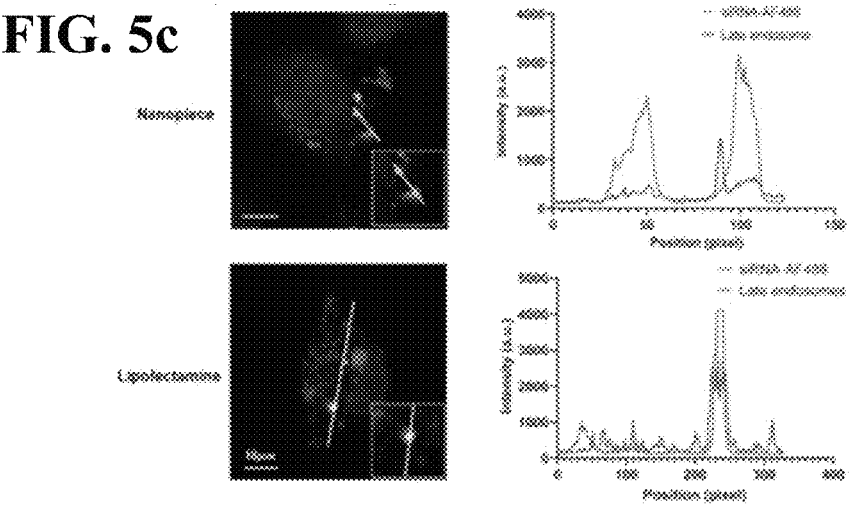
Figure 5D:
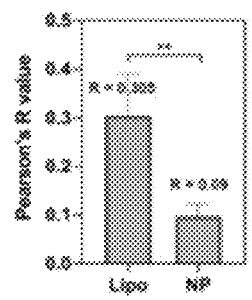

To test the efficiency of the approach described herein, the disclosed JBNPs were compared to a conventional method of gene delivery, Lipofectamine™ 2000 (Lipo). The cells were transfected with NP or Lipo using the same amount of Alexa Fluor®-siRNAs. FIG. 5a shows NPs were better at endosomal escape than Lipo. CLSM images of the delivery of siRNA-Alexa Fluor® 488 by the NP or Lipo; (red, actin), (blue, nuclei), (green, Alexa Fluor®-siRNA) (FIG. 5b), Endosomal escape of the NP and Lipo (FIG. 5c). Colocalization analysis of late endosomes and Alexa Fluor®-siRNA delivered by NP or Lipo following the yellow arrow line. FIG. 5d shows quantification of colocalization by Pearson's R-value.

Figure 6A:
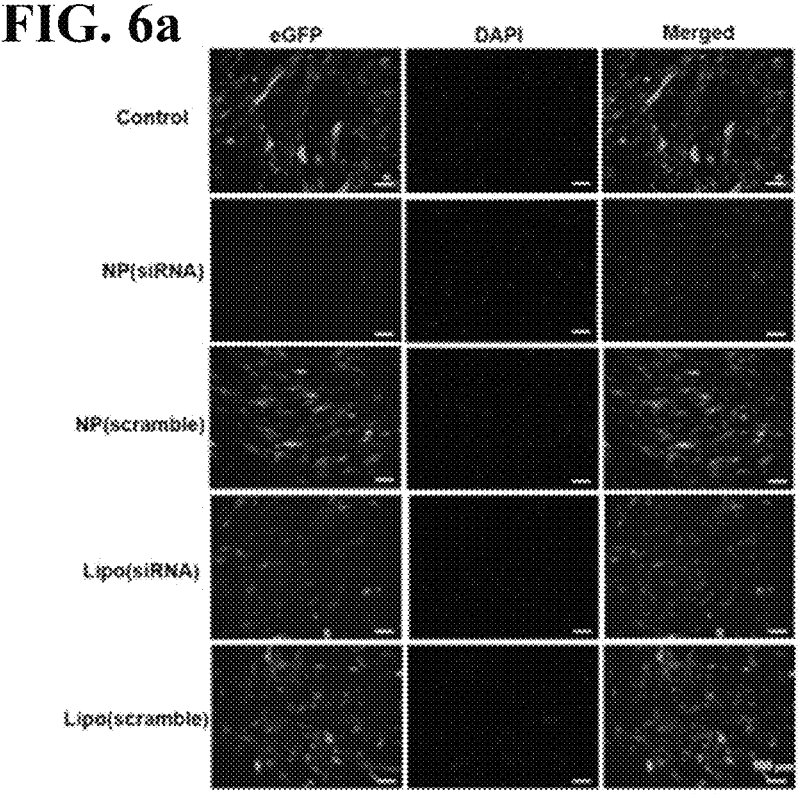
FIGS. 6a-6b show a functional assay of an exemplary JBNP.
Figure 6B:
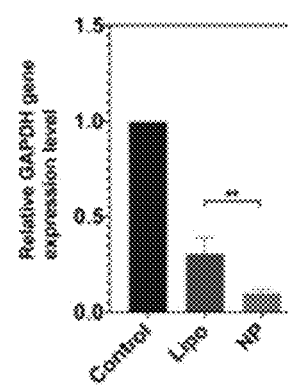

To examine the anti-virus ability of NPs, NP were transfected to demonstrate the antiviral effect by delivering siRNAs. FIG. 6a shows that NPs can effectively inhibit viral gene expression (green fluorescence) and they outperformed Lipo. FIG. 6b shows that the disclosed NP can effectively downregulate the gene expression more than Lipo.

Figure 7:
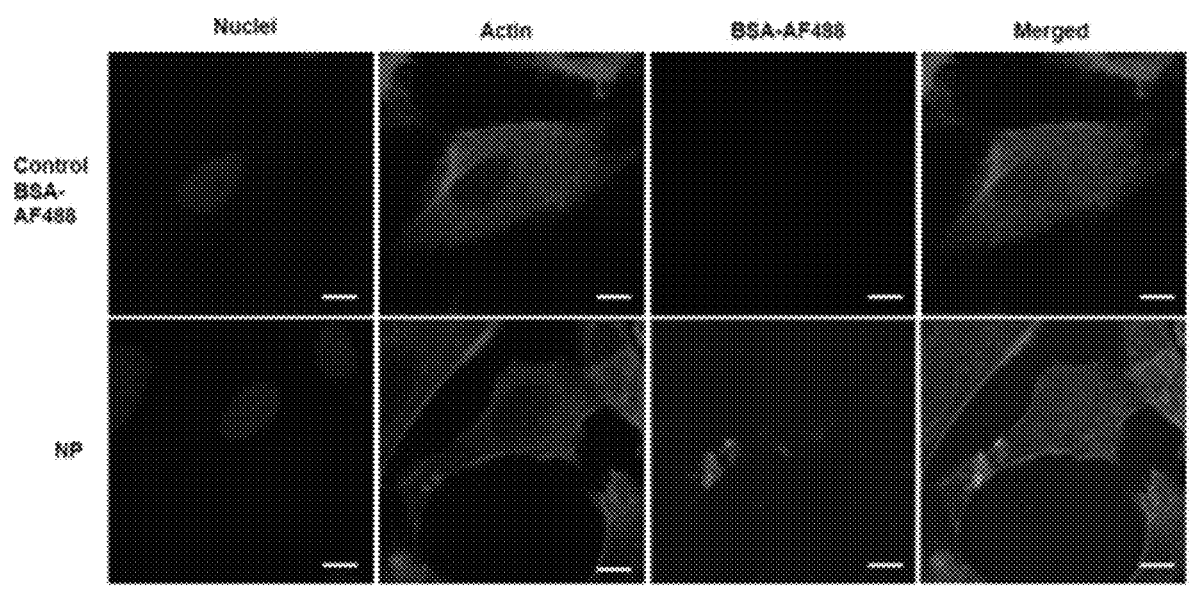
FIG. 7 shows JBNPs successfully delivered protein (BSA) into cells.

FIG. 7 shows NP-protein delivered into SKOV-3 cells. CLSM images of bovine serum albumin (BSA)-Alexa Fluor® 488 delivered to the SKOV-3 cells via NP; stained with nuclei (blue) by DAPI, actin (red) by rhodamine phalloidin, and BSA-Alexa Fluor®-488 (green).

Figures 8A, 8B, 8C, 8D:
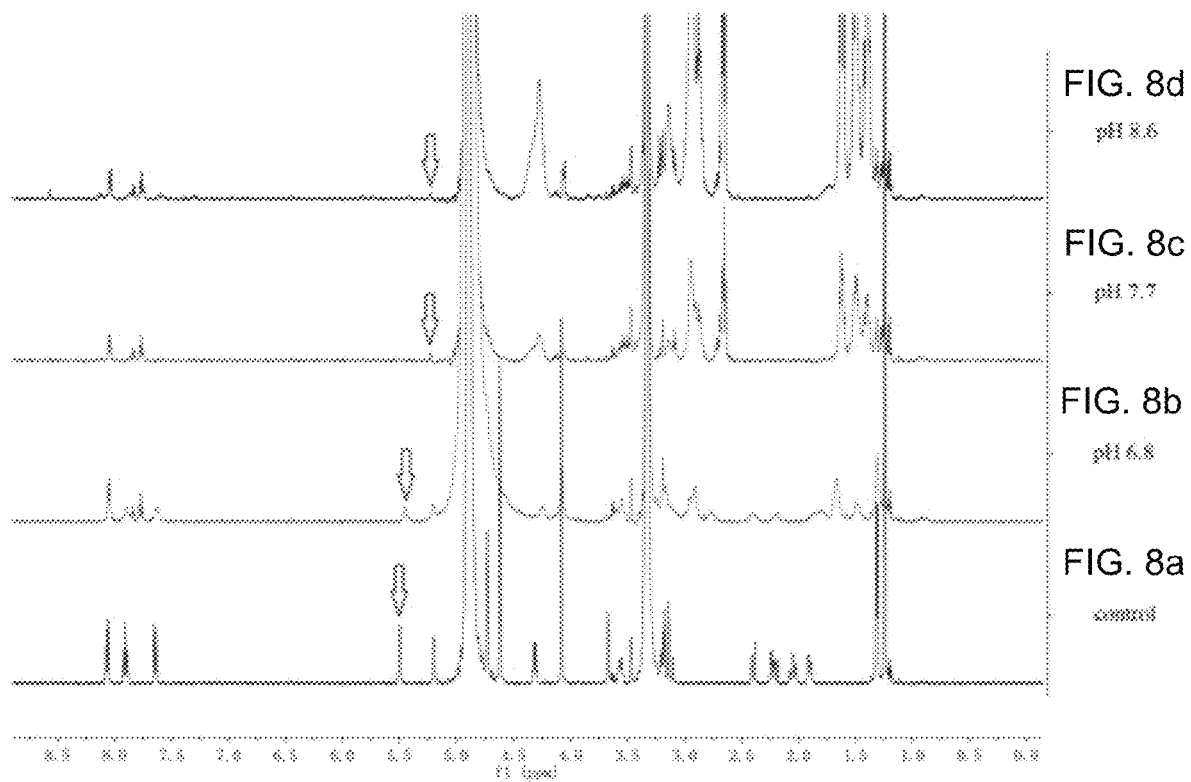
FIGS. 8a-8d show $^1$H NMR spectra of $^1$H NMR spectra of (a) control (DOX) and DOX-JBNT mixtures at different pHs; (b) pH 6.8; (c) pH 7.7; (d) pH 8.6. (arrow points out the Ha peak of DOX demonstrating the loading and unloading of DOX molecules in JBNTs).
Figure 9A:
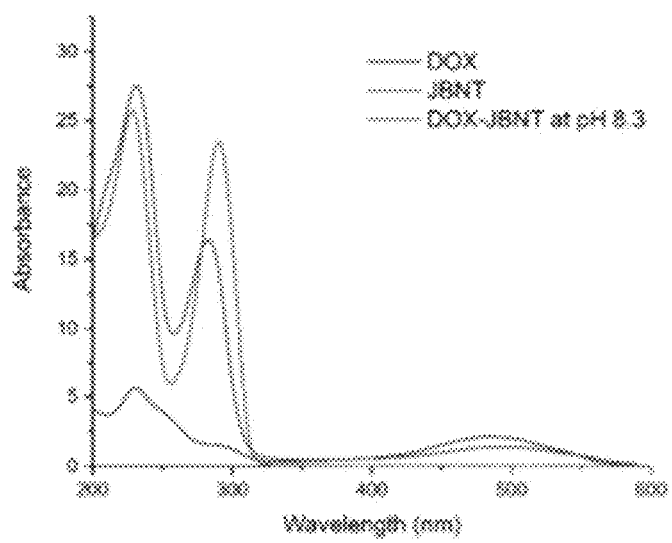
FIGS. 9a-9b show UV-Vis spectra of (a) DOX, JBNT and DOX-JBNT mixture at pH 8.3; (b) DOX-JBNT mixture at different pHs and sum of DOX and JBNT (recorded in water, concentration: DOX 0.1 mg/mL, JBNTs 0.7 mg/mL).
Figure 9B:
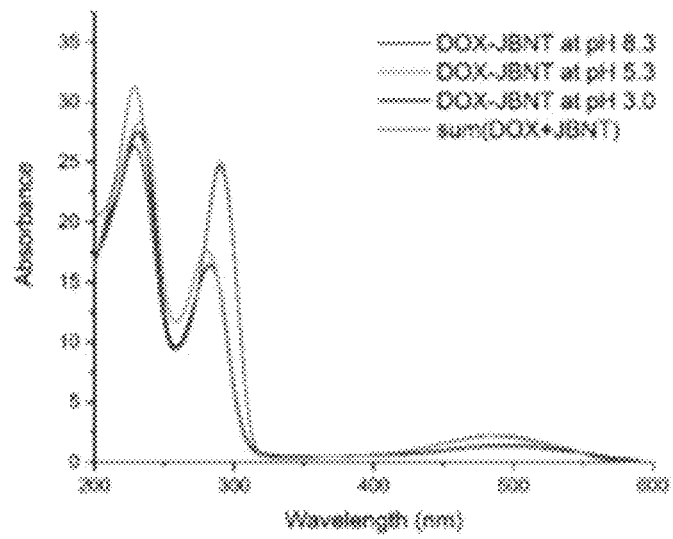
Figure 10:
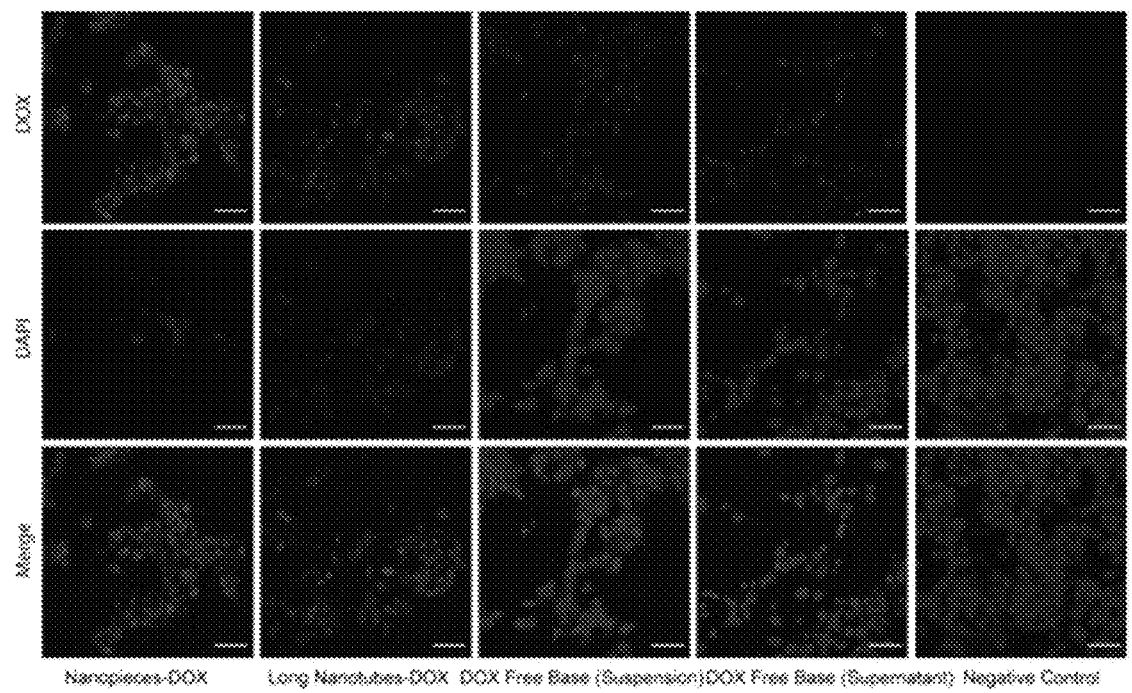
FIG. 10 shows the hydrophobic drug delivered effect.

FIGS. 8-10 show JBNTs successfully delivered small molecule (doxorubicin) into cells. FIG. 8 shows $^1$H NMR spectra of (8a) control (DOX) and DOX-JBNT mixtures at different pHs; (8b) pH 6.8; (8c) pH 7.7; (8d) pH 8.6. (arrow points out the Ha peak of DOX demonstrating the loading and unloading of DOX molecules in JBNTs. FIG. 9 shows UV-Vis spectra of (9a) DOX, JBNT and DOX-JBNT mixture at pH 8.3; (9b) DOX-JBNT mixture at different pHs and sum of DOX and JBNT (recorded in water, concentration: DOX 0.1 mg/mL, JBNTs 0.7 mg/mL). FIG. 10 shows the hydrophobic drug delivered effect. Confocal images of MCF 7 cells after incubation with different groups of materials for 24 h. Scale Bar: 50 µmv.

Figure 11A:
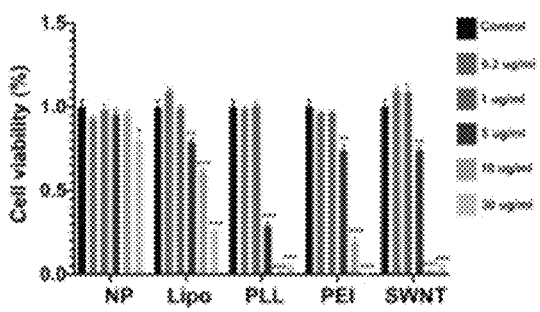
FIGS. 11a-11b show cell viability assay of an exemplary JBNP.
Figure 11B:
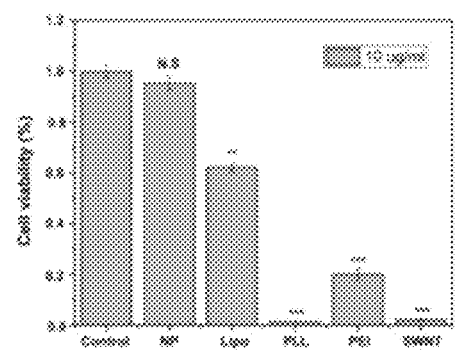

The cytotoxicity of biomaterials is a crucial factor in gene delivery vehicles. As exemplified in FIGS. 11a and b, NP demonstrated the best cell viability compared with other delivery materials: Lipo, polymers (PLL and PEI), and carbon nanotubes (SWNT).

Example 2: Synthesis of JNBTs

All reagents and solvents were obtained from commercial suppliers and used without further purification. Commercial suppliers include Sigma-Aldrich, Alfa Aesar, Fisher Scientific and Thermo Fisher.

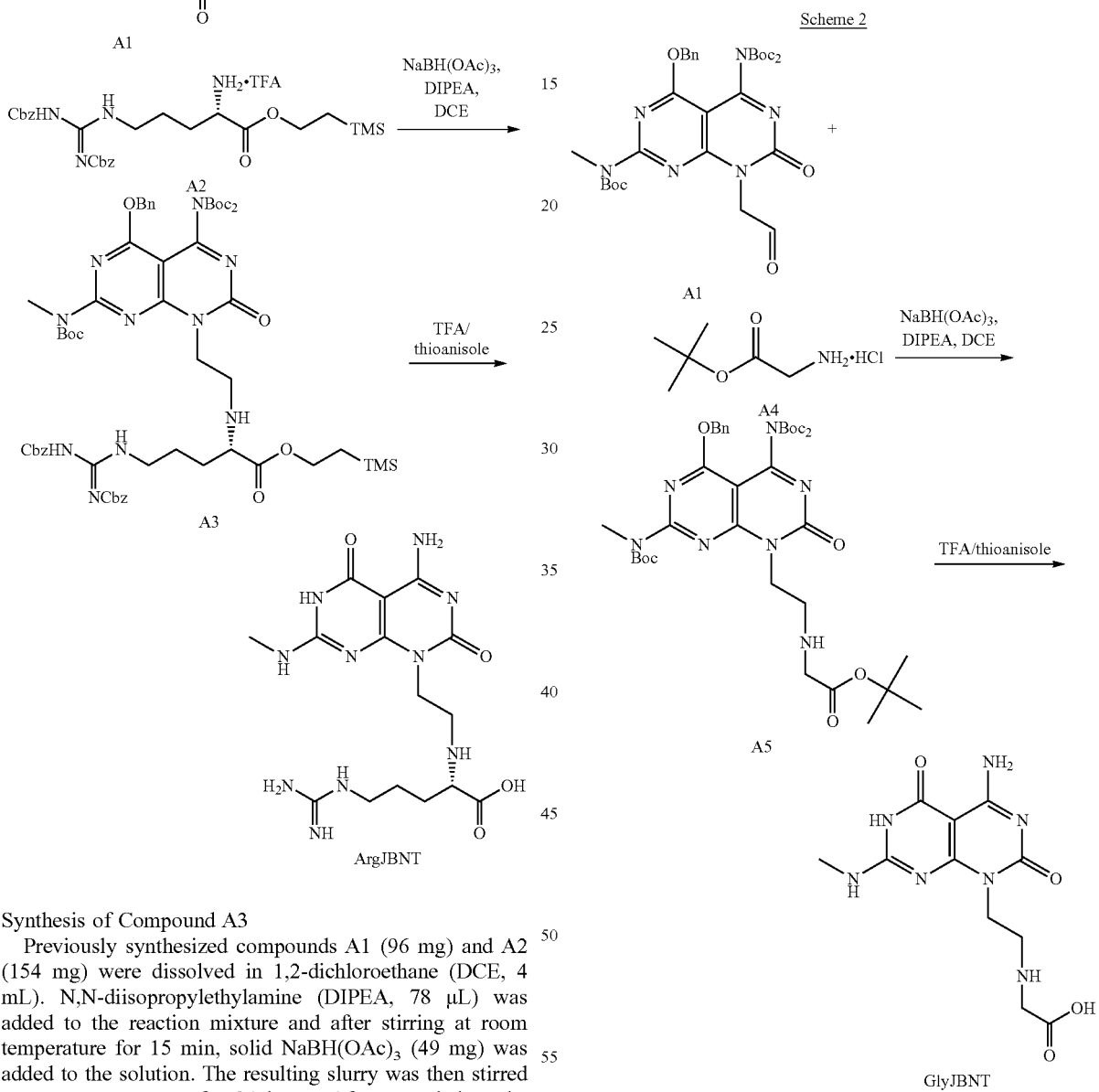

Scheme 1

Scheme 2

Synthesis of Compound A3

Previously synthesized compounds A1 (96 mg) and A2 (154 mg) were dissolved in 1,2-dichloroethane (DCE, 4 mL). N,N-diisopropylethylamine (DIPEA, 78 µL) was added to the reaction mixture and after stirring at room temperature for 15 min, solid NaBH(OAc)$_3$ (49 mg) was added to the solution. The resulting slurry was then stirred at room temperature for 24 hours. After completion, the reaction mixture was quenched with water, and extracted with dichloromethane. The organic layers were combined and washed with brine. After drying over MgSO$_4$, filtration and evaporation of solvent under reduced pressure, the crude product A3 (156 mg) was used in the next step without further purification.

Synthesis of Compound ArgJBNT

Compound A3 (156 mg) was added into 94% TFA/thioanisole (2.8 mL) solution. After stirring at room temperature for 72 hours, diethyl ether (Et$_2$O) was added. A white precipitate formed and was then centrifuged down. After pouring supernatant out, the white precipitate was then washed with Et$_2$O to yield crude product. The crude product was purified using HPLC to produce compound ArgJBNT (37 mg, 70%). $^1$H NMR (500 MHz, DCl/D$_2$O) δ 4.62-4.43 (m, 2H), 4.11 (dd, J=7.4, 4.8 Hz, 1H), 3.58-3.45 (m, 2H), 3.26-3.19 (m, 2H), 3.03 (s, 3H), 2.07-1.94 (m, 2H), 1.80-1.60 (m, 2H). HRMS (ESI) [M+H]$^+$ calculated for 409.2055, found 409.2078.

Synthesis of Compound A5

Previously synthesized compound A1 (96 mg) and commercially available A4 (40 mg) were dissolved in 1,2-dichloroethane (DCE, 4 mL). N,N-diisopropylethylamine (DIPEA, 78 µL) was added to the reaction mixture and after stirring at room temperature for 15 min, solid NaBH(OAc)$_3$ (49 mg) was added to the solution. The resulting slurry was then stirred at room temperature for 24 hours. After completion, the reaction mixture was quenched with water, and extracted with dichloromethane. The organic layers were combined and washed with brine. After drying over MgSO$_4$, filtration and evaporation of solvent under reduced pressure, the crude product A5 (102 mg) was used in the next step without further purification.

Synthesis of Compound GlyJBNT

Compound A5 (102 mg) was added into 94% TFA/thioanisole (2.8 mL) solution. After stirring at room temperature for 72 hours, diethyl ether (Et$_2$O) was added. A white precipitate formed and was then centrifuged down. After pouring supernatant out, the white precipitate was then washed with Et$_2$O to yield crude product. The crude product was purified using HPLC to produce compound GlyJBNT (34 mg, 85%). $^1$H NMR (500 MHz, DMSO-d6) δ 11.83 (br, m, 1H), 8.88 (br, m, 2H), 8.54 (br, m, 1H), 8.13 (br, m, 1H), 7.70 (br, m, 1H), 4.34 (br, m, 2H), 3.88 (br, m, 2H), 3.26 (br, m, 2H), 2.93 (br, m, 3H). HRMS (ESI) [M+H]$^+$ calculated for 310.2158, found 310.1208.

Scheme 3

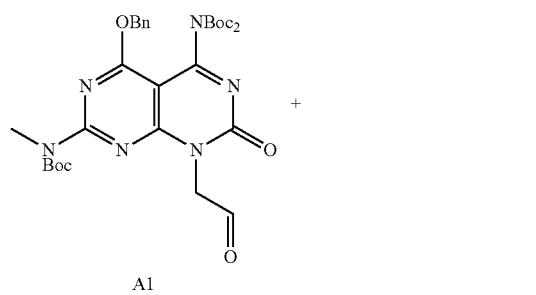

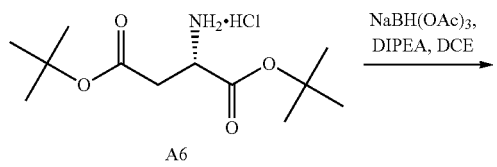

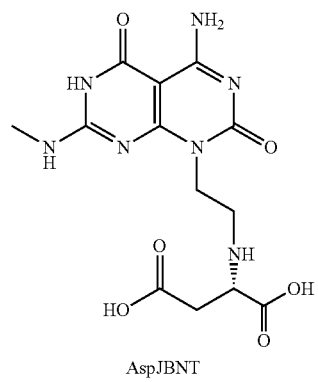

AspJBNT

Synthesis of Compound A7

Previously synthesized compound A1 (96 mg) and commercially available A6 (68 mg) were dissolved in 1,2-dichloroethane (DCE, 4 mL). N,N-diisopropylethylamine (DIPEA, 78 μL) was added to the reaction mixture and after stirring at room temperature for 15 min, solid NaBH(OAc)$_3$ (49 mg) was added to the solution. The resulting slurry was then stirred at room temperature for 24 hours. After completion, the reaction mixture was quenched with water, and extracted with dichloromethane. The organic layers were combined and washed with brine. After drying over MgSO$_4$, filtration and evaporation of solvent under reduced pressure, the crude product A7 (110 mg) was used in the next step without further purification.

Synthesis of Compound AspJBNT

Compound A7 (110 mg) was added into 94% TFA/thioanisole (2.8 mL) solution. After stirring at room temperature for 72 hours, diethyl ether (Et$_2$O) was added. A white precipitate formed and was then centrifuged down. After pouring supernatant out, the white precipitate was then washed with Et$_2$O to yield crude product. The crude product was purified using HPLC to produce compound AspJBNT (47 mg, 98%). $^1$H NMR (500 MHz, DMSO-d6) δ 11.77 (br, m, 1H), 8.51 (br, m, 1H), 8.06 (br, m, 1H), 7.55 (br, m, 1H), 4.34 (br, m, 2H), 4.16 (br, m, 1H), 2.92 (br, m, 3H), 2.85 (br, m, 2H). HRMS (ESI) [M+H]$^+$ calculated for 368.1313, found 368.1278.

Scheme 4

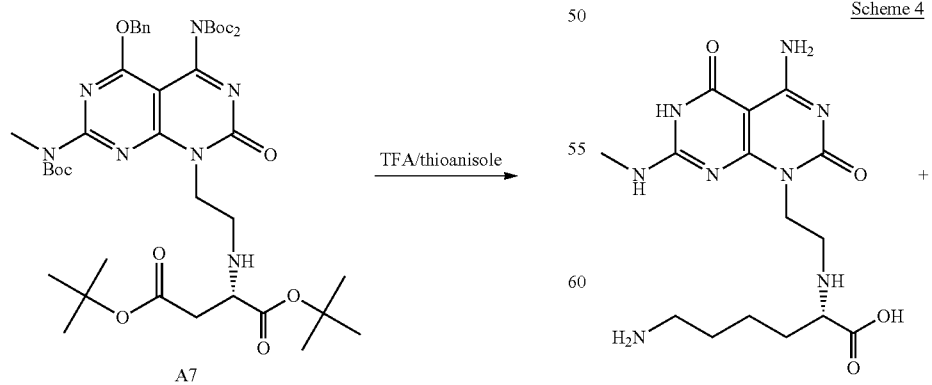

LysJBNT

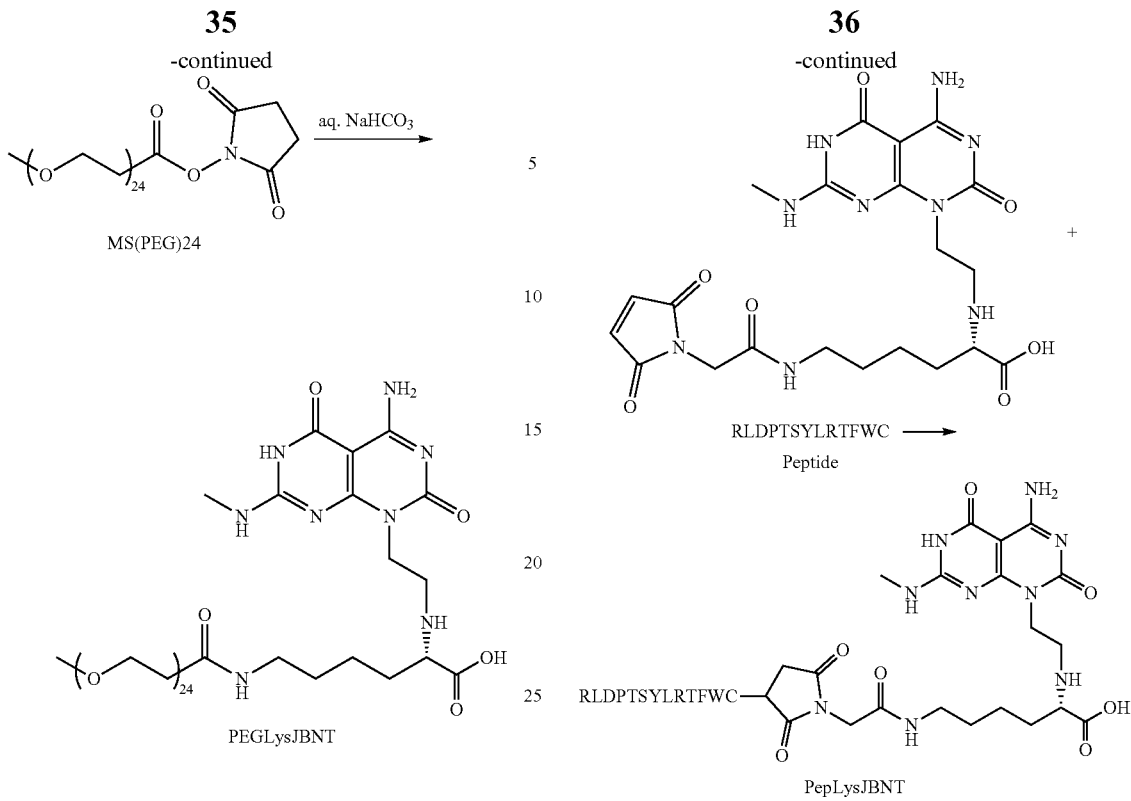

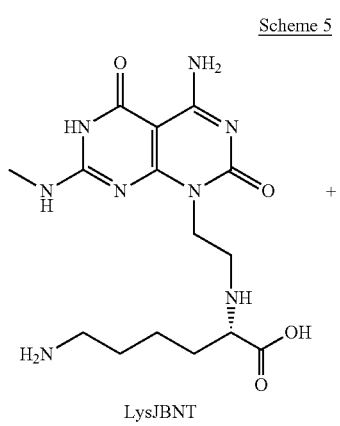

LysJBNT

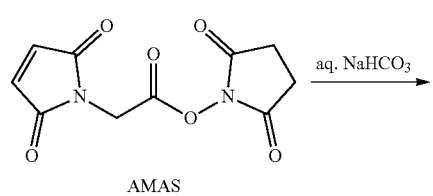

AMAS

Synthesis of Compound PEGLysJBNT

A solution of previous synthesized LysJBNT (1 mg) in aq. NaHCO$_3$ (0.8 mL, 0.01 M) was added to a solution of MS(PEG)24 Methyl-PEG-NHS-Ester (5 mg) in DMF (0.2 mL). After 24 hours, the reaction mixture was purified using HPLC to produce compound PEGLysJBNT (1 mg, 33%). HRMS (ESI) [M+H]$^+$ calculated for 1479.8390, found 1479.8654.

Synthesis of Compound PepLysJBNT

A solution of previous synthesized LysJBNT (1 mg) in aq. NaHCO$_3$ (0.8 mL, 0.01 M) was added to a solution of N-α-maleimidomethyl succinimide ester (AMAS, 1 mg) in DMF (0.2 mL). After 24 hours, peptide (RLDPTSYLRTFWC, 7 mg) was added to the reaction mixture and waited for another 24 hours. The reaction mixture was purified using HPLC to produce compound PepLysJBNT (5 mg, 100%). HRMS (ESI) [M+2H]$^{2+}$ calculated for 1095.5226, found 1095.5038.

Example 3: Co-Assembled JBNTs

Co-assembled JBNTs were prepared by mixing with appropriate molar ratio at room temperature for 24 h self-assembly. For the PEGLys/Arg JBNT, molar ratio of 5% PEGLysJBNTs were mixed with Arg JBNT and self-assembled for 24 h at room temperature. For the PepLys/PEGLys/ArgJBNT, molar ratio of 5% PEGLysJBNT, molar ratio of 5% PepLysJBNT were mixed with Arg JBNT and self-assembled for 24 h at room temperature.

Example 4: Co-Assembled JBNPs

Co-assembled JBNPs were prepared by mixing the cargoes including RNAs, small molecules and proteins with the appropriate molar ratio in nuclease-free water, followed by sonicated with Sonicator (Q Sonica; Sonicators) at the 100% amplitude for 2 min and 30 s.

Example 5: JBNP Characterization

The particles and ζ potential of the JBNPs were measured by dynamic light scattering (Zetasizer) and the morphology was observed by transmission electron microscope (TEM). The gel retardation assay was conducted at 0.8% low-melting agarose gel followed by electrophoresis. The UV- Vis absorption spectra were recorded with a NanoDrop™ One. The buffering capacity of NPs and polymers, NP and cationic polymers at the same 0.08 μmol were titrated by either adding the 2 μL of 10 mM HCl or 10 mM NaOH.

Example 6: JBNP Delivery

Assembled JBNPs were immediately transferred to cells and then incubated at 37° C. and 5% $CO_2$. Then, cells were fixed with 4% formaldehyde, treated with Triton™ X, and stained with rhodamine phalloidin (30 min) and DAPI (10 min). A Nikon A1 confocal laser scanning microscope was used for fluorescence imaging. Uptake of the siRNA-Alexa Fluor®488 was quantified by the flow cytometry after the 24 h or 48 h transfection to the cells. For the siRNA knockdown study, JBNPs was used to deliver GAPDH siRNA for 24 h. Lipofectamine™ 2000 was used as a control according to the manufacturer's protocol. The gene expression was analyzed by RT-PCR.

Example 7: Endosomal Escape Study

For endosomal escape studies, LysoTracker™ Red was used before fixing. The degree of colocalization was quantified based upon Pearson's correlation coefficient (R) using Image J software following the colocalization threshold and coloc2 plugin.

Example 8: Cell Uptake Mechanisms Study

Cells were exposed to several different concentrations of the inhibitors for 1 h, pretreated with Cpz hydrochloride (100 μM for 30 min), Mβcd (1 mM for 30 min), CytD (4 μM for 1 h), Lat (2 μM for 30 min), bafilomycin A1 (200 nM for 30 min), and chloroquine (10 μM for 30 min).

Example 9: Antiviral Study

GFP expressing RGD fiber modified adenovirus was pretreated to the human lung fibroblast cells. JBNPs or LNP containing the eGFP siRNA were transfected for 24 h. A fluorescence microscope was used to take the cell images.

```
                       SEQUENCE LISTING

<160> NUMBER OF SEQ ID NOS: 59

<210> SEQ ID NO 1
<211> LENGTH: 8
<212> TYPE: PRT
<213> ORGANISM: Artificial Sequence
<220> FEATURE:
<223> OTHER INFORMATION: stimuli linkers
<220> FEATURE:
<221> NAME/KEY: X
<222> LOCATION: (5)..(6)
<223> OTHER INFORMATION: pyrrolysine

<400> SEQUENCE: 1

Gly Pro Leu Gly Xaa Ala Gly Gln
1               5

<210> SEQ ID NO 2
<211> LENGTH: 10
<212> TYPE: PRT
<213> ORGANISM: Artificial Sequence
<220> FEATURE:
<223> OTHER INFORMATION: stimuli linker

<400> SEQUENCE: 2

Gly Asp Glu Val Glu Ala Pro Lys Gly Cys
1               5                   10

<210> SEQ ID NO 3
<211> LENGTH: 4
<212> TYPE: PRT
<213> ORGANISM: Artificial Sequence
<220> FEATURE:
<223> OTHER INFORMATION: stimuli linkers

<400> SEQUENCE: 3

Gly Phe Leu Gly
1

<210> SEQ ID NO 4
<211> LENGTH: 6
<212> TYPE: PRT
<213> ORGANISM: Artificial Sequence
```

```
<220> FEATURE:
<223> OTHER INFORMATION: stimuli linkers

<400> SEQUENCE: 4

Ala Leu Ala Leu Phe Lys
1               5

<210> SEQ ID NO 5
<211> LENGTH: 5
<212> TYPE: PRT
<213> ORGANISM: Artificial Sequence
<220> FEATURE:
<223> OTHER INFORMATION: surface targeting modifiers

<400> SEQUENCE: 5

Pro His Ser Arg Asn
1               5

<210> SEQ ID NO 6
<211> LENGTH: 17
<212> TYPE: PRT
<213> ORGANISM: Artificial Sequence
<220> FEATURE:
<223> OTHER INFORMATION: surface targeting modifiers

<400> SEQUENCE: 6

Arg Pro Arg Ala Pro Ala Arg Ser Ala Ser Arg Pro Arg Arg Pro Val
1               5                   10                  15

Glu

<210> SEQ ID NO 7
<211> LENGTH: 16
<212> TYPE: PRT
<213> ORGANISM: Artificial Sequence
<220> FEATURE:
<223> OTHER INFORMATION: surface targeting modifiers

<400> SEQUENCE: 7

Gly Leu Arg Lys Arg Leu Arg Lys Phe Arg Asn Lys Ile Lys Glu Lys
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: surface targeting modifiers

<400> SEQUENCE: 8

Pro Leu Ile Leu Leu Arg Leu Leu Arg Gly Gln Phe
1               5                   10

<210> SEQ ID NO 9
<211> LENGTH: 31
<212> TYPE: PRT
<213> ORGANISM: Artificial Sequence
<220> FEATURE:
<223> OTHER INFORMATION: tumor targeting agents

<400> SEQUENCE: 9

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30
```

```
<210> SEQ ID NO 10
<211> LENGTH: 9
<212> TYPE: PRT
<213> ORGANISM: Artificial Sequence
<220> FEATURE:
<223> OTHER INFORMATION: tumor targeting agents

<400> SEQUENCE: 10

Cys Gly Asn Lys Arg Thr Arg Gly Cys
1               5

<210> SEQ ID NO 11
<211> LENGTH: 5
<212> TYPE: PRT
<213> ORGANISM: Artificial Sequence
<220> FEATURE:
<223> OTHER INFORMATION: tumor targeting agents

<400> SEQUENCE: 11

Cys Arg Glu Lys Ala
1               5

<210> SEQ ID NO 12
<211> LENGTH: 9
<212> TYPE: PRT
<213> ORGANISM: Artificial Sequence
<220> FEATURE:
<223> OTHER INFORMATION: tumor targeting agents

<400> SEQUENCE: 12

Cys Ser Asn Arg Asp Ala Arg Arg Cys
1               5

<210> SEQ ID NO 13
<211> LENGTH: 12
<212> TYPE: PRT
<213> ORGANISM: Artificial Sequence
<220> FEATURE:
<223> OTHER INFORMATION: tumor targeting agents

<400> SEQUENCE: 13

Tyr Cys Asp Gly Phe Tyr Ala Cys Tyr Met Asp Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: tumor targeting agents

<400> SEQUENCE: 14

Lys Gln Phe Ser Ala Leu Pro Phe Asn Phe Tyr Thr
1               5                   10

<210> SEQ ID NO 15
<211> LENGTH: 14
<212> TYPE: PRT
<213> ORGANISM: Artificial Sequence
<220> FEATURE:
<223> OTHER INFORMATION: tumor targeting agents

<400> SEQUENCE: 15

Pro Leu Gly Leu Ala Gly Gly Trp Gly Glu Arg Asp Gly Ser
1               5                   10

<210> SEQ ID NO 16
```

```
<211> LENGTH: 13
<212> TYPE: PRT
<213> ORGANISM: Artificial Sequence
<220> FEATURE:
<223> OTHER INFORMATION: tumor targeting agents

<400> SEQUENCE: 16

Gly Gly Gly Gly Tyr Asp Arg Val Thr Ile His Pro Phe
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Atherosclerotic-related disease targeting
      agents

<400> SEQUENCE: 17

Val His Ser Pro Asn Lys Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Atherosclerotic-related disease targeting
      agents

<400> SEQUENCE: 18

Val His Pro Lys Gln His Arg
1               5

<210> SEQ ID NO 19
<211> LENGTH: 19
<212> TYPE: PRT
<213> ORGANISM: Artificial Sequence
<220> FEATURE:
<223> OTHER INFORMATION: Atherosclerotic-related disease targeting
      agents

<400> SEQUENCE: 19

Val Leu Thr Thr Gly Leu Pro Ala Leu Ile Ser Trp Ile Lys Arg Lys
1               5                   10                  15

Arg Gln Gln

<210> SEQ ID NO 20
<211> LENGTH: 7
<212> TYPE: PRT
<213> ORGANISM: Artificial Sequence
<220> FEATURE:
<223> OTHER INFORMATION: Atherosclerotic-related disease targeting
      agents

<400> SEQUENCE: 20

Asn Asn Ser Lys Ser His Thr
1               5

<210> SEQ ID NO 21
<211> LENGTH: 12
<212> TYPE: PRT
<213> ORGANISM: Artificial Sequence
<220> FEATURE:
<223> OTHER INFORMATION: Atherosclerotic-related disease targeting
      agents

<400> SEQUENCE: 21
```

```
Val His Pro Lys Gln His Arg Ala Glu Glu Ala Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Atherosclerotic-related disease targeting
      agents

<400> SEQUENCE: 22

Cys Asn Asn Ser Lys Ser His Thr Cys Cys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Atherosclerotic-related disease targeting
      agents

<400> SEQUENCE: 23

Val His Pro Lys Gln His Arg Gly Gly Ser Lys Gly Cys
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Atherosclerotic-related disease targeting
      agents

<400> SEQUENCE: 24

Val His Ser Pro Asn Lys Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Atherosclerotic-related disease targeting
      agents

<400> SEQUENCE: 25

Cys Lys Gly Gly Arg Ala Lys Asp Cys
1               5

<210> SEQ ID NO 26
<211> LENGTH: 13
<212> TYPE: PRT
<213> ORGANISM: Artificial Sequence
<220> FEATURE:
<223> OTHER INFORMATION: targeting molecule

<400> SEQUENCE: 26

Cys Gly Phe Glu Cys Val Arg Gln Cys Pro Glu Arg Cys
1               5                   10

<210> SEQ ID NO 27
<211> LENGTH: 6
<212> TYPE: PRT
<213> ORGANISM: Artificial Sequence
<220> FEATURE:
```

<223> OTHER INFORMATION: targeting molecule

<400> SEQUENCE: 27

Ser Glu Lys Asp Glu Leu
1               5

<210> SEQ ID NO 28
<211> LENGTH: 17
<212> TYPE: PRT
<213> ORGANISM: Artificial Sequence
<220> FEATURE:
<223> OTHER INFORMATION: targeting molecule

<400> SEQUENCE: 28

Met Arg Tyr Met Ile Leu Gly Leu Leu Ala Leu Ala Ala Val Cys Ser
1               5                   10                  15

Ala

<210> SEQ ID NO 29
<211> LENGTH: 24
<212> TYPE: PRT
<213> ORGANISM: Artificial Sequence
<220> FEATURE:
<223> OTHER INFORMATION: targeting molecule

<400> SEQUENCE: 29

Arg Gly Asp Cys Cys Cys Cys Gly Gly Asp Lys Leu Ala Lys Leu Ala
1               5                   10                  15

Lys Lys Leu Ala Lys Leu Ala Lys
            20

<210> SEQ ID NO 30
<211> LENGTH: 4
<212> TYPE: PRT
<213> ORGANISM: Artificial Sequence
<220> FEATURE:
<223> OTHER INFORMATION: targeting molecule

<400> SEQUENCE: 30

Phe Arg Phe Lys
1

<210> SEQ ID NO 31
<211> LENGTH: 7
<212> TYPE: PRT
<213> ORGANISM: Artificial Sequence
<220> FEATURE:
<223> OTHER INFORMATION: targeting molecule
<220> FEATURE:
<221> NAME/KEY: X
<222> LOCATION: (2)..(3)
<223> OTHER INFORMATION: dimethyl ornithine
<220> FEATURE:
<221> NAME/KEY: X
<222> LOCATION: (5)..(6)
<223> OTHER INFORMATION: 2'6'-dimethylTyr

<400> SEQUENCE: 31

Arg Xaa Phe Arg Xaa Lys Phe
1               5

<210> SEQ ID NO 32
<211> LENGTH: 30
<212> TYPE: PRT
<213> ORGANISM: Artificial Sequence
<220> FEATURE:
<223> OTHER INFORMATION: targeting molecule

<400> SEQUENCE: 32

Met Ser Val Leu Thr Pro Leu Leu Leu Arg Gly Leu Thr Gly Ser Ala
1               5                   10                  15

Arg Arg Leu Pro Val Pro Arg Ala Lys Ile His Trp Leu Cys
            20                  25                  30

<210> SEQ ID NO 33
<211> LENGTH: 15
<212> TYPE: PRT
<213> ORGANISM: Artificial Sequence
<220> FEATURE:
<223> OTHER INFORMATION: targeting molecule

<400> SEQUENCE: 33

Asp Lys Leu Ala Lys Leu Ala Lys Lys Leu Ala Lys Leu Ala Lys
1               5                   10                  15

<210> SEQ ID NO 34
<211> LENGTH: 6
<212> TYPE: PRT
<213> ORGANISM: Artificial Sequence
<220> FEATURE:
<223> OTHER INFORMATION: targeting molecule

<400> SEQUENCE: 34

Lys Lys Lys Arg Lys Val
1               5

<210> SEQ ID NO 35
<211> LENGTH: 17
<212> TYPE: PRT
<213> ORGANISM: Artificial Sequence
<220> FEATURE:
<223> OTHER INFORMATION: targeting molecule

<400> SEQUENCE: 35

Lys Arg Pro Ala Ala Thr Lys Lys Ala Gly Gln Ala Lys Lys Lys Lys
1               5                   10                  15

Leu

<210> SEQ ID NO 36
<211> LENGTH: 12
<212> TYPE: PRT
<213> ORGANISM: Artificial Sequence
<220> FEATURE:
<223> OTHER INFORMATION: targeting molecule

<400> SEQUENCE: 36

Gly Arg Lys Lys Arg Arg Gln Arg Arg Arg Pro Gln
1               5                   10

<210> SEQ ID NO 37
<211> LENGTH: 8
<212> TYPE: PRT
<213> ORGANISM: Artificial Sequence
<220> FEATURE:
<223> OTHER INFORMATION: targeting molecule

<400> SEQUENCE: 37

Arg Arg Arg Arg Arg Arg Arg Arg
1               5

<210> SEQ ID NO 38
<211> LENGTH: 16

```
<212> TYPE: PRT
<213> ORGANISM: Artificial Sequence
<220> FEATURE:
<223> OTHER INFORMATION: targeting molecule

<400> SEQUENCE: 38

Arg Gln Ile Lys Ile Trp Phe Gln Asn Arg Arg Met Lys Trp Lys Lys
1               5                   10                  15

<210> SEQ ID NO 39
<211> LENGTH: 21
<212> TYPE: PRT
<213> ORGANISM: Artificial Sequence
<220> FEATURE:
<223> OTHER INFORMATION: targeting molecule

<400> SEQUENCE: 39

Gly Asp Ile Met Gly Glu Trp Gly Asn Glu Ile Phe Gly Ala Ile Ala
1               5                   10                  15

Ala Gly Phe Leu Gly
            20

<210> SEQ ID NO 40
<211> LENGTH: 30
<212> TYPE: PRT
<213> ORGANISM: Artificial Sequence
<220> FEATURE:
<223> OTHER INFORMATION: targeting molecule

<400> SEQUENCE: 40

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 41
<211> LENGTH: 7
<212> TYPE: PRT
<213> ORGANISM: Artificial Sequence
<220> FEATURE:
<223> OTHER INFORMATION: targeting molecule

<400> SEQUENCE: 41

Phe Phe Leu Ile Pro Lys Gly
1               5

<210> SEQ ID NO 42
<211> LENGTH: 13
<212> TYPE: PRT
<213> ORGANISM: Artificial Sequence
<220> FEATURE:
<223> OTHER INFORMATION: targeting molecule

<400> SEQUENCE: 42

Thr His Arg Pro Pro Met Trp Ser Pro Val Trp Pro
1               5                   10

<210> SEQ ID NO 43
<211> LENGTH: 19
<212> TYPE: PRT
<213> ORGANISM: Artificial Sequence
<220> FEATURE:
<223> OTHER INFORMATION: targeting molecule

<400> SEQUENCE: 43

Thr Phe Phe Tyr Gly Gly Ser Arg Gly Lys Arg Asn Asn Phe Lys Thr
```

```
1               5                   10                  15

Glu Glu Tyr

<210> SEQ ID NO 44
<211> LENGTH: 16
<212> TYPE: PRT
<213> ORGANISM: Artificial Sequence
<220> FEATURE:
<223> OTHER INFORMATION: targeting molecule

<400> SEQUENCE: 44

Phe Lys Glu Ser Trp Arg Glu Ala Arg Gly Thr Arg Ile Glu Arg Gly
1               5                   10                  15

<210> SEQ ID NO 45
<211> LENGTH: 36
<212> TYPE: PRT
<213> ORGANISM: Artificial Sequence
<220> FEATURE:
<223> OTHER INFORMATION: targeting molecule

<400> SEQUENCE: 45

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
                20                  25                  30

Cys Leu Cys Arg
        35

<210> SEQ ID NO 46
<211> LENGTH: 8
<212> TYPE: PRT
<213> ORGANISM: Artificial Sequence
<220> FEATURE:
<223> OTHER INFORMATION: targeting molecule

<400> SEQUENCE: 46

Asp Leu Ala Thr Glu Pro Ala Leu
1               5

<210> SEQ ID NO 47
<211> LENGTH: 7
<212> TYPE: PRT
<213> ORGANISM: Artificial Sequence
<220> FEATURE:
<223> OTHER INFORMATION: targeting molecule

<400> SEQUENCE: 47

Gly Phe Thr Gly Phe Leu Ser
1               5

<210> SEQ ID NO 48
<211> LENGTH: 29
<212> TYPE: PRT
<213> ORGANISM: Artificial Sequence
<220> FEATURE:
<223> OTHER INFORMATION: targeting molecule

<400> SEQUENCE: 48

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
                20                  25
```

```
<210> SEQ ID NO 49
<211> LENGTH: 11
<212> TYPE: PRT
<213> ORGANISM: Artificial Sequence
<220> FEATURE:
<223> OTHER INFORMATION: targeting molecule

<400> SEQUENCE: 49

Cys Arg Gly Asp Lys Arg Gly Pro Asp Glu Cys
1               5                   10

<210> SEQ ID NO 50
<211> LENGTH: 36
<212> TYPE: PRT
<213> ORGANISM: Artificial Sequence
<220> FEATURE:
<223> OTHER INFORMATION: targeting molecule

<400> SEQUENCE: 50

Thr Ala Met Arg Ala Val Asp Lys Leu Leu His Leu Lys Lys Leu
1               5                   10                  15

Phe Arg Glu Gly Gln Phe Asn Arg Asn Phe Glu Ser Ile Ile Ile Cys
            20                  25                  30

Arg Asp Arg Thr
        35

<210> SEQ ID NO 51
<211> LENGTH: 9
<212> TYPE: PRT
<213> ORGANISM: Artificial Sequence
<220> FEATURE:
<223> OTHER INFORMATION: targeting molecule

<400> SEQUENCE: 51

Cys Gly Glu Met Gly Trp Val Arg Cys
1               5

<210> SEQ ID NO 52
<211> LENGTH: 9
<212> TYPE: PRT
<213> ORGANISM: Artificial Sequence
<220> FEATURE:
<223> OTHER INFORMATION: targeting molecule

<400> SEQUENCE: 52

Cys Gly Asn Lys Arg Thr Arg Gly Cys
1               5

<210> SEQ ID NO 53
<211> LENGTH: 11
<212> TYPE: PRT
<213> ORGANISM: Artificial Sequence
<220> FEATURE:
<223> OTHER INFORMATION: targeting molecule

<400> SEQUENCE: 53

Met Tyr Ile Glu Ala Leu Asp Lys Tyr Ala Cys
1               5                   10

<210> SEQ ID NO 54
<211> LENGTH: 33
<212> TYPE: PRT
<213> ORGANISM: Artificial Sequence
<220> FEATURE:
<223> OTHER INFORMATION: targeting molecule

<400> SEQUENCE: 54
```

```
Pro Lys Lys Lys Arg Lys Val Ala Ala Phe Glu Asp Leu Arg Val Leu
1               5                   10                  15

Ser Lys Arg Pro Ala Ala Thr Lys Lys Arg Gly Gln Arg Lys Lys Lys
                20                  25                  30

Lys

<210> SEQ ID NO 55
<211> LENGTH: 5
<212> TYPE: PRT
<213> ORGANISM: Artificial Sequence
<220> FEATURE:
<223> OTHER INFORMATION: coating materials

<400> SEQUENCE: 55

Cys Ala Leu Asn Asn
1               5

<210> SEQ ID NO 56
<211> LENGTH: 5
<212> TYPE: PRT
<213> ORGANISM: Artificial Sequence
<220> FEATURE:
<223> OTHER INFORMATION: coating materials

<400> SEQUENCE: 56

Cys Cys Val Val Thr
1               5

<210> SEQ ID NO 57
<211> LENGTH: 6
<212> TYPE: PRT
<213> ORGANISM: Artificial Sequence
<220> FEATURE:
<223> OTHER INFORMATION: coating materials

<400> SEQUENCE: 57

Cys Leu Pro Phe Phe Asp
1               5

<210> SEQ ID NO 58
<211> LENGTH: 15
<212> TYPE: PRT
<213> ORGANISM: Artificial Sequence
<220> FEATURE:
<223> OTHER INFORMATION: coating materials

<400> SEQUENCE: 58

Gly Cys Gly Gly Cys Gly Gly Lys Gly Gly Cys Gly Gly Cys Gly
1               5                   10                  15

<210> SEQ ID NO 59
<211> LENGTH: 6
<212> TYPE: PRT
<213> ORGANISM: Artificial Sequence
<220> FEATURE:
<223> OTHER INFORMATION: coating materials

<400> SEQUENCE: 59

His His

We claim:

1. A composition comprising a compound of Formula (I):

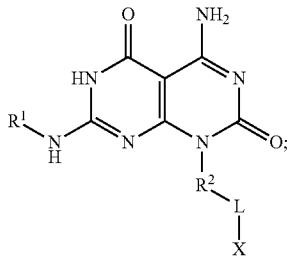
(I)

or a pharmaceutically acceptable salt thereof, wherein:

$R^1$ is H or $CH_3$;

$R^2$ is $(CH_2)_j$, $(CH_2CH_2O)_k$ or $(CH_2CH_2NH)_m$;

j, k, and m are the chemical subscripts for the moieties listed in R2 and each it independently represents 0-200 of the repeating moieties;

L is absent; and

X is folic acid

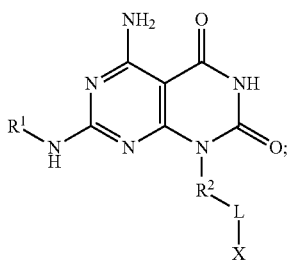

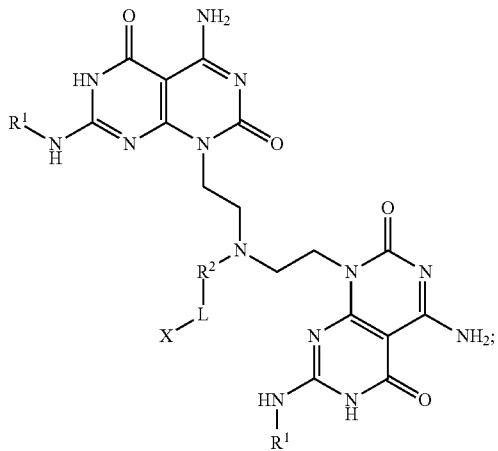
(III)

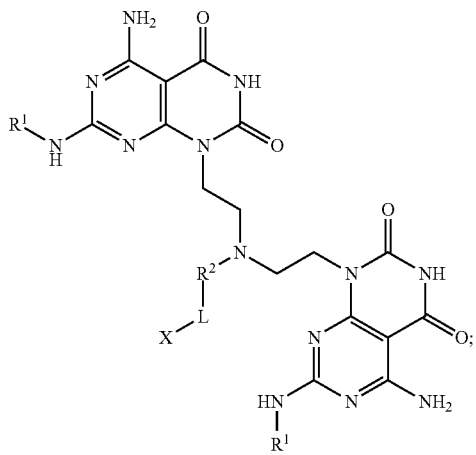
(IV)

wherein the composition has a pH of about 1 to about 10.

2. The composition of claim 1, wherein the therapeutic agent is targeting molecule that is a surface targeting modifier, a membrane dipeptidase targeting molecule, an endoplasmic reticulum (ER) targeting molecule, a mitochondrial membrane targeting molecule, a nucleus targeting molecule.

* * * * *